US005516650A

United States Patent [19]

Foster et al.

[11] Patent Number: 5,516,650

[45] Date of Patent: May 14, 1996

[54] PRODUCTION OF ACTIVATED PROTEIN C

[75] Inventors: Donald C. Foster; Mark J. Murray; Kathleen L. Berkner, all of Seattle, Wash.

[73] Assignee: Zymogenetics, Inc., Seattle, Wash.

[21] Appl. No.: 225,253

[22] Filed: Apr. 8, 1994

Related U.S. Application Data

[63] Continuation of Ser. No. 987,532, Dec. 4, 1992, abandoned, which is a continuation of Ser. No. 582,131, Sep. 10, 1990, abandoned, which is a continuation of Ser. No. 317,205, Feb. 28, 1989, abandoned, which is a continuation-in-part of Ser. No. 130,370, Dec. 8, 1987, abandoned, which is a continuation-in-part of Ser. No. 924,462, Oct. 29, 1986, Pat. No. 4,959,318, which is a continuation-in-part of Ser. No. 749,600, Jun. 27, 1985, abandoned.

[51] Int. Cl.$^6$ .............................. C12P 21/06; C12N 9/50; C12N 5/02; C07H 19/00

[52] U.S. Cl. .................... 435/68.1; 435/69.1; 435/172.3; 435/219; 435/226; 435/240.25; 435/320.1; 536/22.1; 536/23.1; 536/23.2; 536/23.5; 935/14; 935/70; 935/71

[58] Field of Search ................................ 435/68.1, 69.1, 435/172.3, 219, 226, 240.25, 320.1; 536/22.1, 23.1, 23.2, 23.5; 935/14, 70, 71

[56] References Cited

U.S. PATENT DOCUMENTS

| | | | |
|---|---|---|---|
| 4,604,285 | 8/1986 | Smith et al. | 424/94 |
| 4,751,180 | 6/1988 | Cousens et al. | 435/68 |
| 4,770,999 | 11/1988 | Kaufman et al. | 435/68 |
| 4,775,624 | 10/1988 | Bang et al. | 435/226 |
| 4,784,950 | 11/1988 | Hagen et al. | 435/68 |
| 4,959,318 | 9/1990 | Foster et al. | 435/69.1 |
| 5,077,204 | 12/1991 | Brake et al. | 435/68.1 |

FOREIGN PATENT DOCUMENTS

| | | | |
|---|---|---|---|
| 138222 | 4/1985 | European Pat. Off. | C12P 21/00 |
| 245949 | 11/1987 | European Pat. Off. | |
| 296413 | 12/1988 | European Pat. Off. | C12N 15/00 |
| WO85/00521 | 2/1985 | United Kingdom | A61K 35/16 |
| WO88/03926 | 11/1986 | WIPO | C12P 21/00 |

OTHER PUBLICATIONS

Foster et al., Proc. Natl. Acad. Sci. U.S.A. 81:4766–4770 (1984).
Beckmann et al., Nuc. Acids Res., 13: 5233–5247 (Jul., '85).
Thomas et al., *Science 241:* 226–230, 1988.
Marx, *Science 235:* 285–286, 1987.
Bathurst et al., *Science 235:* 348–350, 1987.
Dmochowska et al., *Cell 50:*573–584, 1987.
Fuller et al., in Leive, ed., *Microbiology:1986,* 273–278.
Foster et al., *Proc. Natl. Acad. Sci. USA 81:*4766–4770, 1984.
Taylor et al., *J. Clin. Invest 79:*918–925, 1987.
Kisiel et al., *Biochem 16:*5824–5831, 1977.
Long et al., *PNAS 81:*5653–5656, 1984.
Walker et al., *Biochim et Biophys. Acta 571:*333–342, 1979.
Beckmann et al., *Fed. Proc. 44:*3951, 1985.
Katayama et al., *PNAS 76:* 4990–4994, 1979.
McMullen et al., *Biochem. and Biophys. Res. Comm. 115:*8–14, 1983.
Miletech and Broze, "Characterization of Monoclonal Antibody Specific for the Heavy Chain of Non–Activated Human Protein C," Nov. 1983.
Kisiel and Davie, *Methods in Enzymology 80:*320–332, 1981.
Griffin et al., *J. Clin. Invest. 68:*1370–1373, 1981.
Van Hinsbergh et al., *Blood 65:*444–451, 1985.
Kisiel et al., *Behring Inst. Mitt. 73:*29–43, 1983.
Gardiner et al., *Prog. Hematol 13:*265–278, 1983.
Comp et al., *J. Clin. Invest., 68:*1221–1228, 1981.
Sakata et al., *PNAS 82:*1121–1125, 1985.
Broekmans et al., *New Eng. Journ. Med. 309:*340–344, 1983.
Seligsohn et al., *New Eng. Journ. Med. 310:*559–562,1984.
Marlar et al., *Blood 59:*1067–1072, 1982.
Foster et al. *PNAS 82:*4673–4677, 1985.
Kaufman and Sharp, *Mol. and Cell. Biol. 2:*1304–1319, 1982.
Kisiel, *J. Clin. Invest. 64:*761–769, 1979.
Kaufman, *PNAS 82:*689–693, 1985.
Hermonat et al., *PNAS 81:*6466–6470, 1984.
Ginsburg et al., *Science 228:*1401–1406, 1985.
Plutzky et al., *PNAS 83:*546–550, 1986.
Esmon et al., *PNAS 78:*2249–2252, 1981.
Degan et al., *Biochemistry 22:*2087–2092, 1983.
Stenflo et al., *J. Biochem. 257:*12180–12190, 1982.
Fernlund et al., *J. Biochem 257:*12170–12179, 1982.
Foster et al., *Thromb. Haemostatis 58:*230, 1987.
Foster et al. *Biochemistry 26:*7003–7011, 1987.
Busby et al., *Current Advances in Vitamin K Research* (1988), 173–181.
Berkner et al. *Current Advances in Vitamin K Research* (1988), 199–207.
Leytus et al., *Biochemistry 25:*5098–5102, 1986.
Grinnell et al., *Bio/Technology 5:*1189, 1987.
Ehrlich et al., *Blood 70:*386a, 1987.
Gruber et al., *Arteriosclerosis 8:*673a, 1988.
Gruber et al., *Circulation 78* (4 part 2):II–313, 1988.
Yan et al., *FASEB J. 2:*A1412, 1988.
Yan and Grinell, *Fed Proc. 46:*2243, 1987.
Beckmann et al. *Nuc. Acids. Res.* 13:5233–5247 (Jul. '85).

*Primary Examiner*—Robert A. Wax
*Assistant Examiner*—Hyosuk Kim
*Attorney, Agent, or Firm*—Seed and Berry

[57] ABSTRACT

Methods are disclosed for producing a protein which has substantially the same biological activity as human protein C or human activated protein C. The protein is produced by mammalian host cells transfected with a plasmid capable of integration in mammalian host cell DNA. The plasmid includes a promoter followed downstream by a nucleotide sequence which encodes a protein having substantially the same structure and/or activity as human protein C or human activated protein C the nucleotide sequence being followed downstream by a polyadenylation signal.

52 Claims, 16 Drawing Sheets

```
GGCTGTCATG GCGGCAGGAC GGCGAACTTG CAGTATCTCC ACGACCCGCC CCTGTGCCAG TGCCTCCAG

-42      -40                                         -30
ATG TGG CAG CTC ACA AGC CTC CTG CTG TTC GTG GCC ACC TGG GGA ATT TCC GGC
MET Trp Gln Leu Thr Ser Leu Leu Leu Phe Val Ala Thr Trp Gly Ile Ser Gly

                    -20                                     -10
ACA CCA GCT CCT CTT GAC TCA GTG TTC TCC AGC AGC GAG CGT GCC CAC CAG GTG
Thr Pro Ala Pro Leu Asp Ser Val Phe Ser Ser Ser Glu Arg Ala His Gln Val

                        -1  +1                             10
CTG CGG ATC CGC AAA CGT GCC AAC TCC TTC CTG GAG GAG CTC CGT CAC AGC AGC
Leu Arg Ile Arg Lys Arg Ala Asn Ser Phe Leu Glu Glu Leu Arg His Ser Ser

                            20                                      30
CTG GAG CGG GAG TGC ATA GAG GAG ATC TGT GAC TTC GAG GAG GCC AAG GAA ATT
Leu Glu Arg Glu Cys Ile Glu Glu Ile Cys Asp Phe Glu Glu Ala Lys Glu Ile

                                    40
TTC CAA AAT GTG GAT GAC ACA CTG GCC TTC TGG TCC AAG CAC GTC GAC GGT GAC
Phe Gln Asn Val Asp Asp Thr Leu Ala Phe Trp Ser Lys His Val Asp Gly Asp

    50                                      60
CAG TGC TTG GTC TTG CCC TTG GAG CAC CCG TGC GCC AGC CTG TGC TGC GGG CAC
Gln Cys Leu Val Leu Pro Leu Glu His Pro Cys Ala Ser Leu Cys Cys Gly His

            70                                      80
GGC ACG TGC ATC GAC GGC ATC GGC AGC TTC AGC TGC GAC TGC CGC AGC GGC TGG
Gly Thr Cys Ile Asp Gly Ile Gly Ser Phe Ser Cys Asp Cys Arg Ser Gly Trp

                        90                              ✦       100
GAG GGC CGC TTC TGC CAG CGC GAG GTG AGC TTC CTC AAT TGC TCG CTG GAC AAC
Glu Gly Arg Phe Cys Gln Arg Glu Val Ser Phe Leu Asn Cys Ser Leu Asp Asn

                            110                                     120
GGC GGC TGC ACG CAT TAC TGC CTA GAG GAG GTG GGC TGG CGG CGC TGT AGC TGT
Gly Gly Cys Thr His Tyr Cys Leu Glu Glu Val Gly Trp Arg Arg Cys Ser Cys

                                    130
GCG CCT GGC TAC AAG CTG GGG GAC GAC CTC CTG CAG TGT CAC CCC GCA GTG AAG
Ala Pro Gly Tyr Lys Leu Gly Asp Asp Leu Leu Gln Cys His Pro Ala Val Lys

    140                                     150
TTC CCT TGT GGG AGG CCC TGG AAG CGG ATG GAG AAG AAG CGC AGT CAC CTG AAA
Phe Pro Cys Gly Arg Pro Trp Lys Arg Met Glu Lys Lys Arg Ser His Leu Lys

            160                                     170
CGA GAC ACA GAA GAC CAA GAA GAC CAA GTA GAT CCG CGG CTC ATT GAT GGG AAG
Arg Asp Thr Glu Asp Gln Glu Asp Gln Val Asp Pro Arg Leu Ile Asp Gly Lys
```

*Fig. 2A*

```
                    180                                     190
ATG ACC AGG CGG GGA GAC AGC CCC TGG CAG GTG GTC CTG CTG GAC TCA AAG AAG
Met Thr Arg Arg Gly Asp Ser Pro Trp Gln Val Val Leu Leu Asp Ser Lys Lys

                        200                                         210
AAG CTG GCC TGC GGG GCA GTG CTC ATC CAC CCC TCC TGG GTG CTG ACA GCG GCC
Lys Leu Ala Cys Gly Ala Val Leu Ile His Pro Ser Trp Val Leu Thr Ala Ala

                                220
CAC TGC ATG GAT GAG TCC AAG AAG CTC CTT GTC AGG CTT GGA GAG TAT GAC CTG
His Cys Met Asp Glu Ser Lys Lys Leu Leu Val Arg Leu Gly Glu Tyr Asp Leu

    230                                 240
CGG CGC TGG GAG AAG TGG GAG CTG GAC CTG GAC ATC AAG GAG GTC TTC GTC CAC
Arg Arg Trp Glu Lys Trp Glu Leu Asp Leu Asp Ile Lys Glu Val Phe Val His

    ✦       250                                     260
CCC AAC TAC AGC AAG AGC ACC ACC GAC AAT GAC ATC GCA CTG CTG CAC CTG GCC
Pro Asn Tyr Ser Lys Ser Thr Thr Asp Asn Asp Ile Ala Leu Leu His Leu Ala

                    270                                     280
CAG CCC GCC ACC CTC TCG CAG ACC ATA GTG CCC ATC TGC CTC CCG GAC AGC GGC
Gln Pro Ala Thr Leu Ser Gln Thr Ile Val Pro Ile Cys Leu Pro Asp Ser Gly

                        290                                         300
CTT GCA GAG CGC GAG CTC AAT CAG GCC GGC CAG GAG ACC CTC GTG ACG GGC TGG
Leu Ala Glu Arg Glu Leu Asn Gln Ala Gly Gln Glu Thr Leu Val Thr Gly Trp

                                310         ✦
GGC TAC CAC AGC AGC CGA GAG AAG GAG GCC AAG AGA AAC CGC ACC TTC GTC CTC
Gly Tyr His Ser Ser Arg Glu Lys Glu Ala Lys Arg Asn Arg Thr Phe Val Leu

    320                                 ✦ 330
AAC TTC ATC AAG ATT CCC GTG GTC CCG CAC AAT GAG TGC AGC GAG GTC ATG AGC
Asn Phe Ile Lys Ile Pro Val Val Pro His Asn Glu Cys Ser Glu Val Met Ser

            340                                     350
AAC ATG GTG TCT GAG AAC ATG CTG TGT GCG GGC ATC CTC GGG GAC CGG CAG GAT
Asn Met Val Ser Glu Asn Met Leu Cys Ala Gly Ile Leu Gly Asp Arg Gln Asp

                    360                                     370
GCC TGC GAG GGC GAC AGT GGG GGG CCC ATG GTC GCC TCC TTC CAC GGC ACC TGG
Ala Cys Glu Gly Asp Ser Gly Gly Pro Met Val Ala Ser Phe His Gly Thr Trp

                        380                                         390
TTC CTG GTG GGC CTG GTG AGC TGG GGT GAG GGC TGT GGG CTC CTT CAC AAC TAC
Phe Leu Val Gly Leu Val Ser Trp Gly Glu Gly Cys Gly Leu Leu His Asn Tyr

                                400
GGC GTT TAC ACC AAA GTC AGC CGC TAC CTC GAC TGG ATC CAT GGG CAC ATC AGA
Gly Val Tyr Thr Lys Val Ser Arg Tyr Leu Asp Trp Ile His Gly His Ile Arg
```

*Fig. 2B*

```
    410                                      419
GAC AAG GAA GCC CCC CAG AAG AGC TGG GCA CCT TAG CGACCCTCCC TGCAGGGCTG
Asp Lys Glu Ala Pro Gln Lys Ser Trp Ala Pro

GGCTTTTGCA TGGCAATGGA TGGGACATTA AAGGGACATG TAACAAGCAC ACCGGCCTGC TGTTCTGTCC

TTCCATCCCT CTTTTGGGCT CTTCTGGAGG GAAGTAACAT TTACTGAGCA CCTGTTGTAT GTCACATGCC

TTATGAATAG AATCTTAACT CCTAGAGCAA CTCTGTGGGG TGGGGAGGAG CAGATCCAAG TTTTGCGGGG

TCTAAAGCTG TGTGTGTTGA GGGGGATACT CTGTTTATGA AAAAGAATAA AAAACACAAC CACGAAAAAA
```

*Fig. 2C*

```
AGTGAATCTG GGCGAGTAAC ACAAAACTTG AGTGTCCTTA CCTGAAAAAT AGAGGTTAGA GGGATGCTAT GTGCCATTGT GTGTGTGTGT TGGGGGTGGG GATTGGGGGT GATTTGTGAG CAATTGGAGG -2001
TGAGGGTGGA GCCCAGTGCC CAGCACCTAT GCACTGGGGA CCCAAAAAGG AGCATCTTCT CATGATTTTA TGTATCAGAA ATTGGGATGG CATGTCATTG GGACAGCGTC TTTTTTCTTG TATGGTGGCA -1871
CATAAATACA TGTGTCTTAT AATTAATGGT ATTTTAGATT TGACGAAATA TGGAATATTA CCTGTTGTGC TGATCTTGGG CAAACTATAA TATCTCTGGG CAAAAATGTC CCCATCTGAA AAACAGGGAC -1741
AACGTTCCTC CCTCAGCCAG CCACTATGGG GCTAAAATGA GACCACATCT GTCAAGGGTT TTGCCCTCAC CTCCCTCCCT GCTGGATGGC ATCCTTGGTA GGCAGAGGTG GGCTTCGGGC AGAACAAGCC -1611
GTGCTGAGCT AGGACCAGGA GTGCTAGTGC CACTGTTTGT CTATGGAGAG GGAGGCCTCA GTGCTGAGGG CCAAGCAAAT ATTTGTGGTT ATGGATTAAC TCGAACTCCA GGCTGTCATG GCGGCAGGAC -1481
GGCGAACTTG CAGTATCTCC ACGACCCGCC CCTGTGAGTC CCCCTCCAGG CAGGTCTATG AGGGGTGTGG AGGGAGGGCT GCCCCCGGGA GAAGAGAGCT AGGTGGTGAT GAGGGCTGAA TCCTCCAGCC -1351
AGGGTGCTCA ACAAGCCTGA GCTTGGGGTA AAAGGACACA AGGCCCTCCA CAGGCCAGGC CTGGCAGCCA CAGTCTCAGG TCCCTTTGCC ATGCGCCTCC CTCTTTCCAG GCCAAGGGTC CCCAGGCCCA -1221
GGGCCATTCC AACAGACAGT TTGGAGCCCA GGACCCTCCA TTCTCCCCAC CCCACTTCCA CCTTTGGGGG TGTCGGATTT GAACAAATCT CAGAAGCGGC CTCAGAGGGA GTCGGCAAGA ATGGAGAGCA -1091
GGGTCCGGTA GGGTGTGCAG AGGCCACGTG GCCTATCCAC TGGGGAGGGT TCCTTGATCT CTGGCCACCA GGGCTATCTC TGTGGCCTTT TGGAGCAACC TGGTGGTTTG GGGCAGGGGT TGAATTTCCA -961
GGCCTAAAAC CACACAGGCC TGGCCTTGAG TCCTGGCTCT GCGAGTAATG CATGGATGTA AACATGGAGA CCCAGGACCT TGCCTCAGTC TTCCGAGTCT GGTGCCTGCA GTGTACTGAT GGTGTAAGAC -831
CCTACTCCTG GAGGATGGGG GACAGAATCT GATCGATCCC CTGGGTTGGT GACTTCCCTG TGCAATCAAC GGAGACCAGC AAGGGTTGGA TTTTTAATAA ACCACTTAAC TCCTCCGAGT CTCAGTTTCC -701
CCCTCTATGA AATGGGGTTG ACAGCATTAA TAACTACCTC TTGGGTGGTT GTGAGCCTTA ACTGAAGTCA TAATATCTCA TGTTTACTGA GCATGAGCTA TGTGCAAAGC CTGTTTTGAG AGCTTTATGT -571
GGACTAACTC CTTTAATTCT CACAACACCC TTTAAGGCAC AGATACACCA CGTTATTCCA TCCATTTTAC AAATGAGGAA ACTGAGGCAT GGAGCAGTTA AGCATCTTGC CCAACATTGC CCTCCAGTAA -441
GTGCTGGAGC TGGAATTTGC ACCGTGCAGT CTGGCTTCAT GGCCTGCCCT GTGAATCCTG TAAAAATTGT TTGAAAGACA CCATGAGTGT CCAATCAACG TTAGCTAATA TTCTCAGCCC AGTCATCAGA -311
CCGGCAGAGG CAGCCACCCC ACTGTCCCCA GGGAGGACAC AAACATCCTG GCACCCTCTC CACTGCATTC TGGAGCTGCT TTCTAGGCAG GCAGTGTGAG CTCAGCCCCA CGTAGAGCGG GCAGCCGAGG -181
CCTTCTGAGG CTATGTCTCT AGCGAACAAG GACCCTCAAT TCCAGCTTCC GCCTGACGGC CAGCACACAG GGACAGCCCT TTCATTCCGC TTCCACCTGG GGGTGCAGGC AGAGCAGCAG CGGGGGTAGC -51
                                                      -42
                                                      Met Trp Gln Leu Thr Ser Leu Leu Leu Phe Val Ala Thr Trp Gly Ile Ser Gly Thr Pro Ala
ACTGCCCGGA GCTCAGAAGT CCTCCTCAGA CAGGTGCCAG TGCCTCCAGA ATG TGG CAG CTC ACA AGC CTC CTG CTG TTC GTG GCC ACC TGG GGA ATT TCC GGC ACA CCA GCT 63
   -20
Pro Leu
CCT CTT G▼GTAAGGCCAC CCCACCCCTA CCCCGGGACC CTTGTGGCCT CTACAAGGCC CTGGTGGCAT CTGCCCAGGC CTTCACAGCT TCCACCATCT CTCTGAGCCC TGGGTGAGGT GAGGGGCAGA 190

TGGGAATGGC AGGAATCAAC TGACAAGTCC CAGGTAGGCC AGCTGCCAGA GTGCCACACA GGGGCTGCCA GGGCAGGCAT GCGTGATGGC AGGGAGCCCC GCGATGACCT CCTAAAGCTC CCTCCTCCAC 320
ACGGGGATGG TCACAGAGTC CCCTGGGCCT TCCCTCTCCA CCCACTCACT CCCTCAACTG TGAAGACCCC AGGCCCAGGC TACCGTCCAC ACTATCCAGC ACAGCCTCCC CTACTCAAAT GCACACTGGC 450
CTCATGGCTG CCCTGCCCCA ACCCCTTTCC TGGTCTCCAC AGCCAACGGG AGGAGGCCAT GATTCTTGGG GAGGTCCGCA GGCACATGGG CCCCTAAAGC CACACCAGGC TGTTGGTTTC ATTTGTGCCT 580
TTATAGAGCT GTTTATCTGC TTGGGACCTG CACCTCCACC CTTTCCCAAG GTGCCCTCAG CTCAGGCATA CCCTCCTCTA GGATGCCTTT TCCCCCATCC CTTCTTGCTC ACACCCCCAA CTTGATCTCT 710
CCCTCCTAAC TGTGCCCTGC ACCAAGACAG ACACTTCACA GAGCCCAGGA CACACCTGGG GACCCTTCCT GGGTGATAGG TCTGTCTATC CTCCAGGTGT CCCTGCCCAA GGGGAGAAGC ATGGGGAATA 840
CTTGGTTGGG GGAGGAAAGG AAGACTGGGG GGATGTGTCA AGATGGGGCT GCATGTGGTG TACTGGCAGA AGAGTGAGAG GATTTAACTT GGCAGCCTTT ACAGCAGCAG CCAGGGCTTG AGTACTTATC 970
TCTGGGCCAG GCTGTATTGG ATGTTTTACA TGACGGTCTC ATCCCCATGT TTTTGGATGA GTAAATTGAA CCTTAGAAAG GTAAAGACAC TGGCTCAAGG TCACACAGAG ATCGGGGTGG GGTTCACAGG 1100
GAGGCCTGTC CATCTCAGAG CAAGGCTTCG TCCTCCAACT GCCATCTGCT TCCTGGGGAG GAAAAGAGCA GAGGACCCCT GCGCCAAGCC ATGACCTAGA ATTAGAATGA GTCTTGAGGG GGCGGAGACA 1230
                                                                                                                           -19
                                                                                                                           Asp Ser Val Phe Ser Ser Ser
AGACCTTCCC AGGCTCTCCC AGCTCTGCTT CCTCAGACCC CCTCATGGCC CCAGCCCCTC TTAGGCCCCT CACCAAGGTG AGCTCCCCTC CCTCCAAAAC CAG▼AC TCA GTG TTC TCC AGC AGC 1353
```

*Fig. 4A*

```
                                    -1  +1
Glu Arg Ala His Gln Val Leu Arg Ile Arg Lys Arg Ala Asn Ser Phe Leu Glu Glu Leu Arg His Ser Ser Leu Glu Arg Glu Cys Ile Glu Glu Ile Cys Asp
GAG CGT GCC CAC CAG GTG CTG CGG ATC CGC AAA CGT GCC AAC TCC TTC CTG GAG GAG CTC CGT CAC AGC AGC CTG GAG CGG GAG TGC ATA GAG GAG ATC TGT GAC   1458
                                                  37
    Phe Glu Glu Ala Lys Glu Ile Phe Gln Asn Val Asp Asp Thr
    TTC GAG GAG GCC AAG GAA ATT TTC CAA AAT GTG GAT GAC ACA▼GTAAGGCCAC CATGGGTCCA GAGGATGAGG CTCAGGGGCG AGCTCGTAAC CAGCAGGGGC CTCGAGGAGC   1570
AGGTGGGGAC TCAATGCTGA GGCCCTCTTA GGAGTTGTGG GGGTGGCTGA GTGGAGCGAT TAGGATGCTG GCCCTATGAT GTCGGCCAGG CACATGTGAC TGCAAGAAAC AGAATTCAGG AAGAAGCTCC   1700
AGGAAAGAGT GTGGGGTGAC CCTAGGTGGG GACTCCCACA GCCACAGTGT AGGTGGTTCA GTCCACCCTC CAGCCACTGC TGAGCACCAC TGCCTCCCCG TCCCACCTCA CAAAGAGGGG ACCTAAAGAC   1830
CACCCTGCTT CCACCCATGC CTCTGCTGAT CAGGGTGTGT GTGTGACCGA AACTCACTTC TGTCCACATA AAATCGCTCA CTCTGTGCCT CACATCAAAG GGAGAAAATC TGATTGTTCA GGGGGTCGGA   1960
AGACAGGGTC TGTGTCCTAT TTGTCTAAGG GTCAGAGTCC TTTGGAGCCC CCAGAGTCCT GTGGACGTGG CCCTAGGTAG TAGGGTGAGC TTGGTAACGG GGCTGGCTTC CTGAGACAAG GCTCAGACCC   2090
GCTCTGTCCC TGGGGATCGC TTCAGCCACC AGGACCTGAA AATTGTGCAC GCCTGGGCCC CCTTCCAAGG CATCCAGGGA TGCTTTCCAG TGGAGGCTTT CAGGGCAGGA GACCCTCTGG CCTGCACCCT   2220
CTCTTGCCCT CAGCCTCCAC CTCCTTGACT GGACCCCCAT CTGGACCTCC ATCCCCACCA CCTCTTTCCC CAGTGGCCTC CCTGGCAGAC ACCACAGTGA CTTTCTGCAG GCACATATCT GATCACATCA   2350
AGTCCCCACC GTGCTCCCAC CTCACCCATG GTCTCTCAGC CCCAGCAGCC TTGGCTGGCC TCTCTGATGG AGCAGGCATC AGGCACAGGC CGTGGGTCTC AACGTGGGCT GGGTGGTCCT GGACCAGCAG   2480
CAGCCGCCGC AGCAGCAACC CTGGTACCTG GTTAGGAACG CAGACCCTCT GCCCCCATCC TCCCAACTCT GAAAAACACT GGCTTAGGGA AAGGCGCGAT GCTCAGGGGT CCCCCAAAGC CCGCAGGCAG   2610
AGGGAGTGAT GGGACTGGAA GGAGGCCGAG TGACTTGGTG AGGGATTCGG GTCCCTTGCA TGCAGAGGCT GCTGTGGGAG CGGACAGTCG CGAGAGCAGC ACTGCAGCTG CATGGGGAGA GGGTGTTGCT   2740
CCAGGGACGT GGGATGGAGG CTGGGCGCGG GCGGGTGGCG CTGGAGGGCG GGGGAGGGGC AGGGAGCACC AGCTCCTAGC AGCCAACGAC CATCGGGCGT CGATCCCTGT TTGTCTGGAA GCCCTCCCCT   2870
                                                                                                                   38                   45
                                                                                                                 Leu Ala Phe Trp Ser Lys His Val
CCCCTGCCCG CTCACCCGCT GCCCTGCCCC ACCCGGGCGC GCCCCTCCGC ACACCGGCTG CAGGAGCCTG ACGCTGCCCG CTCTCTCCGC AG▼CTG GCC TTC TGG TCC AAG CAC GTC G▼GTGAGT   2993
                                                                                                 46
                                                                                                 Asp Gly Asp Gln Cys Leu Val Leu Pro Leu Glu
GCGTTCTAGA TCCCCGGCTG GACTACCGGC GCCCGCGCCC CTCGGGATCT CTGGCCGCTG ACCCCCTACC CCGCCTTGTG TCGCAG▼ AC GGT GAC CAG TGC TTG GTC TTG CCC TTG GAG   3111
                                                                                                                                      91
His Pro Cys Ala Ser Leu Cys Cys Gly His Gly Thr Cys Ile Asp Gly Ile Gly Ser Phe Ser Cys Asp Cys Arg Ser Gly Trp Glu Gly Arg Phe Cys Gln Arg
CAC CCG TGC GCC AGC CTG TGC TGC GGG CAC GGC ACG TGC ATC GAC GGC ATC GGC AGC TTC AGC TGC GAC TGC CGC AGC GGC TGG GAG GGC CGC TTC TGC CAG CGC   3216
                                                                                                                   92                  ✦
                                                                                                                   Glu Val Ser Phe Leu Asn
G▼GTGAGGG GGAGAGGTGG ATGCTGGCGG GCGGCGGGGC GGGGCTGGGG CCGGGTTGGG GGCGCGGCAC CAGCACCAGC TGCCCGCGCC CTCCCCTGCC CGCAG▼ AG GTG AGC TTC CTC AAT   3336

Cys Ser Leu Asp Asn Gly Gly Cys Thr His Tyr Cys Leu Glu Glu Val Gly Trp Arg Arg Cys Ser Cys Ala Pro Gly Tyr Lys Leu Gly Asp Asp Leu Leu Gln
TGC TCT CTG GAC AAC GGC GGC TGC ACG CAT TAC TGC CTA GAG GAG GTG GGC TGG CGG CGC TGT AGC TGT GCG CCT GGC TAC AAG CTG GGG GAC GAC CTC CTG CAG   3440
         136
  Cys His Pro Ala
  TGT CAC CCC GCA G▼GTGAGAAGCC CCCAATACAT CGCCCAGGAA TCACGCTGGG TGCGGGGTGG GCAGGCCCCT GACGGGCGCG GCGCGGGGGG CTCAGGAGGG TTTCTAGGGA GGGAGCGAGG   3564
AACAGAGTTG AGCCTTGGGG CAGCGGCAGA CGCGCCCAAC ACCGGGGCCA CTGTTAGCGC AATCAGCCCG GGAGCTGGGC GCGCCCTCCG CTTTCCCTGC TTCCTTTCTT CCTGGCGTCC CCGCTTCCTC   3694
CGGGCGCCCC TGCGACCTGG GGCCACCTCC TGGAGCGCAA GCCCAGTGGT GGCTCCGCTC CCCAGTCTGA GCGTATCTGG GGCGAGGCGT GCAGCGTCCT CCTCCATGTA GCCTGGCTGC GTTTTTCTCT   3824
GACGTTGTCC GGCGTGCATC GCATTTCCCT CTTTACCCCC TTGCTTCCTT GAGGAGAGAA CAGAATCCCG ATTCTGCCTT CTTCTATATT TTCCTTTTTA TGCATTTTAA TCAAATTTAT ATATGTATGA   3954
```

*Fig. 4B*

```
AACTTTAAAA ATCAGAGTTT TACAACTCTT ACACTTTCAG CATGCTGTTC CTTGGCATGG GTCCTTTTTT CATTCATTTT CATAAAAGGT GGACCCTTTT AATGTGGAAA TTCCTATCTT CTGCCTCTAG 4084
GGCATTTATC ACTTATTTCT TCTACAATCT CCCCTTTACT TCCTCTATTT TCTCTTTCTG GACCTCCCAT TATTCAGACC TCTTTCCTCT AGTTTTATTG TCTCTTCTAT TTCCCATCTC TTTGACTTTG 4214
TGTTTTCTTT CAGGGAACTT TCTTTTTTTT CTTTTTTTTT GAGATGGAGT TTCACTCTTG TTGTCCCAGG CTGGAGTGCA ATGACGTGAT CTCAGCTCAC CACAACCTCC GCCTCCTGGA TTCAAGCGAT 4344
TCTCCTGCCG CAGCCTCCCG AGTAGCTGGG ATTACAGGCA TGCGCCACCA CGCCCAGCTA ATTTTGTGTT TTTAGTAGAG AAGGGGTTTC TCCGTGTTGG TCAAGCTGGT CTTGAACTCC TGACCTCAGG 4474
TGATCCACCT GCCTTGGCCT CCTAAAGTGC TGGGATTACA GGCGTGAGCC ACCGCGCCCA GCCTCTTTCA GGGAACTTTC TACAACTTTA TAATTCAATT CTTCTGCAGA AAAAAATTTT TGGCCAGGCT 4604
CAGTAGCTCA GACCAATAAT TCCAGCACTT TGAGAGGCTG AGGTGGGAGG ATTGCTTGAG CTTGGGAGTT TGAGACTAGC CTGGGCAACA CAGTGAGACC CTGTCTCTAT TTTTAAAAAA AGTAAAAAAA 4734
GATCTAAAAA TTTAACTTTT TATTTTGAAA TAATTTGATA TTTCCAGGAA GCTGCAAAGA AATGCCTGGT GGGCCTGTTG GCTGTGGGTT TCCTGCAAGG CCGTGGGAAG GCCCTGTCAT TGGCAGAACC 4864
CCAGATCGTG AGGGCTTTCC TTTTAGGCTG CTTTCTAAGA GGACTCCTCC AAGCTCTTGG AGGATGGAAG ACGCTCACCC ATGGTGTTCG GCCCCTCAGA GCAGGGTGGG GCAGGGGAGC TGGTGCCTGT 4994
GCAGGCTGTG GACATTTGCA TGACTCCCTG TGGTCAGCTA AGAGCACCAC TCCTTCCTGA AGCGGGGCCT GAAGTCCCTA GTCAGAGCCT CTGGTTCACC TTCTGCAGGC AGGGAGAGGG GAGTCAAGTC 5124
AGTGAGGAGG GCTTTCGCAG TTTCTCTTAC AAACTCTCAA CATGCCCTCC CACCTGCACT GCCTTCCTGG AAGCCCCACA GCCTCCTATG GTTCCGTGGT CCAGTCCTTC AGCTTCTGGG CGCCCCCATC 5254
ACGGGCTGAG ATTTTTGCTT TCCAGTCTGC CAAGTCAGTT ACTGTGTCCA TCCATCTGCT GTCAGCTTCT GGAATTGTTG CTGTTGTGCC CTTTCCATTC TTTTGTTATG ATGCAGCTCC CCTGCTGACG 5384
ACGTCCCATT GCTCTTTTAA GTCTAGATAT CTGGACTGGG CATTCAAGGC CCATTTTGAG CAGAGTCGGG CTGACCTTTC AGCCCTCAGT TCTCCATGGA GTATGCGCTC TCTTCTTGGC AGGGAGGCCT 5514
CACAAACATG CCATGCCTAT TGTAGGAGCT CTCCAAGAAT GCTCACCTCC TTCTCCCTGT AATTCCTTTC CTCTGTGAGG AGCTCAGCAG CATCCCATTA TGAGACCTTA CTAATCCCAG GGATCACCCC 5644
CAACAGCCCT GGGGTACAAT GAGCTTTTAA GAAGTTTAAC CACCTATGTA AGGAGACACA GGCAGTGGGC GATGCTGCCT GGCCTGACTC TTGCCATTGG GTGGTACTGT TTGTTGACTG ACTGACTGAC 5774
TGACTGGAGG GGGTTTGTAA TTTGTATCTC AGGGATTACC CCCAACAGCC CTGGGGTACA ATGAGCCTTC AAGAAGTTTA ACAACCTATG TAAGGACACA CAGCCAGTGG GTGATGCTGC CTGGTCTGAC 5904
TCTTGCCATT CAGTGGCACT GTTTGTTGAC TGACTGACTG ACTGACTGGC TGACTGGAGG GGGTTCATAG CTAATATTAA TGGAGTGGTC TAAGTATCAT TGGTTCCTTG AACCCTGCAC TGTGGCAAAG 6034

                                                                                                  137
                                                                                                  Val Lys Phe Pro Cys Gly Arg Pro Trp Lys Arg
TGGCCCACAG GCTGGAGGAG GACCAAGACA GGAGGGCAGT CTCGGGAGGA GTGCCTGGCA GGCCCCTCAC CACCTCTGCC TACCTCAG TG AAG TTC CCT TGT GGG AGG CCC TGG AAG CGG 6154

Met Glu Lys Lys Arg Ser His Leu Lys Arg Asp Thr Glu Asp Gln Glu Asp Gln Val Asp Pro Arg Leu Ile Asp Gly Lys Met Thr Arg Arg Gly Asp Ser Pro
ATG GAG AAG AAG CGC AGT CAC CTG AAA CGA GAC ACA GAA GAC CAA GAA GAC CAA GTA GAT CCG CGG CTC ATT GAT GGG AAG ATG ACC AGG CGG GGA GAC AGC CCC 6259
    184
 Trp Gln
 TGG CAG GTGGGAGGCG AGGCAGCACC GGCTCGTCAC GTGCTGGGTC CGGGATCACT GAGTCCATCC TGGCAGCTAT GCTCAGGGTG CAGAAACCGA GAGGGAAGCG CTGCCATTGC GTTTGGGGGA 6385
TGATGAAGGT GGGGGATGCT TCAGGGAAAG ATGGACGCAA CCTGAGGGGA GAGGAGCAGC CAGGGTGGGT GAGGGGAGGG GCATGGGGGC ATGGAGGGGT CTGCAGGAGG GAGGGTTACA GTTTCTAAAA 6515
AGAGCTGGAA AGACACTGCT CTGCTGGCGG GATTTTAGGC AGAAGCCCTG CTGATGGGAG AGGGCTAGGA GGGAGGGCCG GGCTGAGTA CCCCTCCAGC CTCCACATGG GAACTGACAC TTACTGGGTT 6645
CCCCTCTCTG CCAGGCATGG GGGAGATAGG AACCAACAAG TGGGAGTATT TGCCCTGGGG ACTCAGACTC TGCAAGGGTC AGGACCCCAA AGACCCGGCA GCCCAGTGGG ACCACAGCCA GGACGGCCCT 6775
TCAAGATAGG GGCTGAGGGA GGCCAAGGGG AACATCCAGG CAGCCTGGGG GCCACAAAGT CTTCCTGGAA GACACAAGGC CTGCCAAGCC TCTAAGGATG AGAGGAGCTC GCTGGGCGAT GTTGGTGTGG 6905
CTGAGGGTGA CTGAAACAGT ATGAACAGTG CAGGAACAGC ATGGGCAAAG GCAGGAAGAC ACCCTGGGAC AGGCTGACAC TGTAAAATGG GCAAAAATAG AAAACGCCAG AAAGGCCTAA GCCTATGCCC 7035
                                                                                                                            185
                                                                                                                           Val Val Leu Leu Asp Ser Lys
ATATGACCAG GGAACCCAGG AAAGTGCATA TGAAACCCAG GTGCCCTGGA CTGGAGGCTG TCAGGAGGCA GCCCTGTGAT GTCATCATCC CACCCCATTC CAGY GTG GTC CTG CTG GAC TCA AAG 7159
                                                                                                  o                               223
Lys Lys Leu Ala Cys Gly Ala Val Leu Ile His Pro Ser Trp Val Leu Thr Ala Ala His Cys Met Asp Glu Ser Lys Lys Leu Leu Val Arg Leu
AAG AAG CTG GCC TGC GGG GCA GTG CTC ATC CAC CCC TCC TGG GTG CTG ACA GCG GCC CAC TGC ATG GAT GAG TCC AAG AAG CTC CTT GTC AGG CTT G GTATGGGCTG 7266
GAGCCAGGCA GAAGGGGGCT GCCAGAGGCC TGGGTAGGGG GACCAGGCAG GCTGTTCAGG TTTGGGGGAC CCCGCTCCCC AGGTGCTTAA GCAAGAGGCT TCTTGAGCTC CACAGAAGGT GTTTGGGGGG 7396
```

*Fig. 4C*

```
AAGAGGCCTA TGTGCCCCCA CCCTGCCCAC CCATGTACAC CCAGTATTTT GCAGTAGGGG GTTCTCTGGT GCCCTCTTCG AATCTGGGCA CAGGTACCTG CACACACATG TTTGTGAGGG GCTACACAGA 7526
CCTTCACCTC TCCACTCCCA CTCATGAGGA GCAGGCTGTG TGGGCCTCAG CACCCTTGGG TGCAGAGACC AGCAAGGCCT GGCCTCAGGG CTGTGCCTCC CACAGACTGA CAGGGATGGA GCTGTACAGA 7656
GGGAGCCCTA GCATCTGCCA AAGCCACAAG CTGCTTCCCT AGCAGGCTGG GGGCTCCTAT GCATTGGCCC CGATCTATGG CAATTTCTGG AGGGGGGGTC TGGCTCAACT CTTTATGCCA AAAAGAAGGC 7786
AAAGCATATT GAGAAAGGCC AAATTCACAT TTCCTACAGC ATAATCTATG CCAGTGGCCC CGTGGGGCTT GGCTTAGAAT TCCCAGGTGC TCTTCCCAGG GAACCATCAG TCTGGACTGA GAGGACCTTC 7916
TCTCTCAGGT GGGACCCGGC CCTGTCCTCC CTGGCAGTGC CGTGTTCTGG GGGTCCTCCT CTCTGGGTCT CACTGCCCCT GGGGTCTCTC CAGCTACCTT TGCTCCATGT TCCTTTGTGG CTCTGGTCTG 8046
TGTCTGGGGT TTCCAGGGGT CTCGGGCTTC CCTGCTGCCC ATTCCTTCTC TGGTCTCACG GCTCCGTGAC TCCTGAAAAC CAACCAGCAT CCTACCCCTT TGGATTGACA CCTGTTGGCC ACTCCTTCTG 8176
GCAGGAAAAG TCACCGTTGA TAGGGTTCCA CGGCATAGAC AGGTGGCTCC GCGCCAGTGC CTGGGACGTG TGGGTGCACA GTCTCCGGGT GAACCTTCTT CAGGCCCTCT CCCAGGCCTG CAGGGGCACA 8306

                                                                                                          224
                                                                                                          Gly Glu Tyr Asp Leu Arg Arg Trp Glu Lys Trp Glu Leu Asp
CCAGTGGGTG GGCCTCAGGA AAGTGCCACT GGGGAGAGGC TCCCCGCAGC CCACTCTGAC TGTGCCCTCT GCCCTGCAG GA GAG TAT GAC CTG CGG CGC TGG GAG AAG TGG GAG CTG GAC 8426

                                        ◆                            ○
Leu Asp Ile Lys Glu Val Phe Val His Pro Asn Tyr Ser Lys Ser Thr Thr Asp Asn Asp Ile Ala Leu Leu His Leu Ala Gln Pro Ala Thr Leu Ser Gln Thr
CTG GAC ATC AAG GAG GTC TTC GTC CAC CCC AAC TAC AGC AAG AGC ACC ACC GAC AAT GAC ATC GCA CTG CTC CAC CTG GCC CAG CCC GCC ACC CTC TCG CAG ACC 8531

Ile Val Pro Ile Cys Leu Pro Asp Ser Gly Leu Ala Glu Arg Glu Leu Asn Gln Ala Gly Gln Glu Thr Leu Val Thr Gly Trp Gly Tyr His Ser Ser Arg Glu
ATA GTG CCC ATC TGC CTC CCG GAC AGC GGC CTT GCA GAG CGC GAG CTC AAT CAG GCC GGC CAG GAG ACC CTC GTG ACG GGC TGG GGC TAC CAC AGC AGC CGA GAG 8636

                    ◆                                                          ◆
Lys Glu Ala Lys Arg Asn Arg Thr Phe Val Leu Asn Phe Ile Lys Ile Pro Val Val Pro His Asn Glu Cys Ser Glu Val Met Ser Asn Met Val Ser Glu Asn
AAG GAG GCC AAG AGA AAC CGC ACC TTC GTC CTC AAC TTC ATC AAG ATT CCC GTG GTC CCG CAC AAT GAG TGC AGC GAG GTC ATG AGC AAC ATG GTG TCT GAG AAC 8741

                                                            ○
Met Leu Cys Ala Gly Ile Leu Gly Asp Arg Gln Asp Ala Cys Glu Gly Asp Ser Gly Gly Pro Met Val Ala Ser Phe His Gly Thr Trp Phe Leu Val Gly Leu
ATG CTG TGT GCG GGC ATC CTC GGG GAC CGG CAG GAT GCC TGC GAG GGC GAC AGT GGG GGG CCC ATG GTC GCC TCC TTC CAC GGC ACC TGG TTC CTG GTG GGC CTG 8846

Val Ser Trp Gly Glu Gly Cys Gly Leu Leu His Asn Tyr Gly Val Tyr Thr Lys Val Ser Arg Tyr Leu Asp Trp Ile His Gly His Ile Arg Asp Lys Glu Ala
GTG AGC TGG GGT GAG GGC TGT GGG CTC CTT CAC AAC TAC GGC GTT TAC ACC AAA GTC AGC CGC TAC CTC GAC TGG ATC CAT GGG CAC ATC AGA GAC AAG GAA GCC 8951
                              419
Pro Gln Lys Ser Trp Ala Pro STOP
CCC CAG AAG AGC TGG GCA CCT TAG  CGACCCTCCC TGCAGGGCTG GGCTTTTGCA TGGCAATGGA TGGGACATTA AAGGGACATG TAACAAGCAC ACCGGCCTGC TGTTCTGTCC TTCCATCCCT 9075
CTTTTGGGCT CTTCTGGAGG GAAGTAACAT TTACTGAGCA CCTGTTGTAT GTCACATGCC TTATGAATAG AATCTTAACT CCTAGAGCAA CTCTGTGGGG TGGGGAGGAG CAGATCCAAG TTTTGCGGGG 9205

TCTAAAGCTG TGTGTGTTGA GGGGGATACT CTGTTTATGA AAAAGAATAA AAAACACAAC CACGAAGCCA CTAGAGCCTT TTCCAGGGCT TTGGGAAGAG CCTGTGCAAG CCGGGGATGC TGAAGGTGAG 9335

GCTTGACCAG CTTTCCAGCT AGCCCAGCTA TGAGGTAGAC ATGTTTAGCT CATATCACAG AGGAGGAAAC TGAGGGGTCT GAAAGGTTTA CATGGTGGAG CCAGGATTCA AATCTAGGTC TGACTCCAAA 9465
ACCCAGGTGC TTTTTTCTGT TCTCCACTGT CCTGGAGGAC AGCTGTTTCG ACGGTGCTCA GTGTGGAGGC CACTATTAGC TCTGTAGGGA AGCAGCCAGA GACCCAGAAA GTGTTGGTTC AGCCCAGAAT 9595
```

*Fig. 4D*

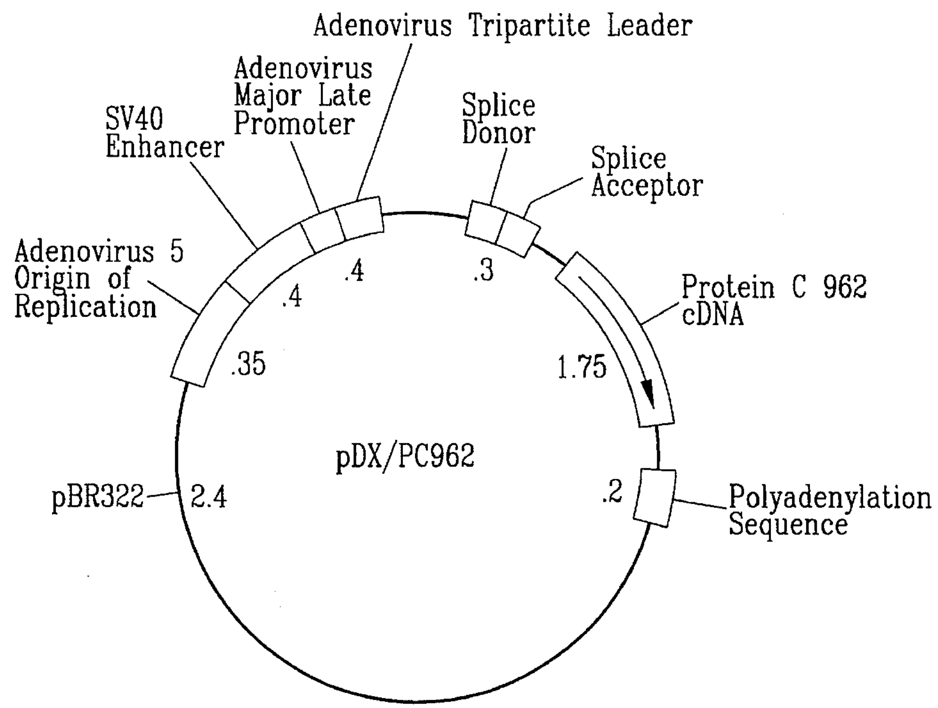
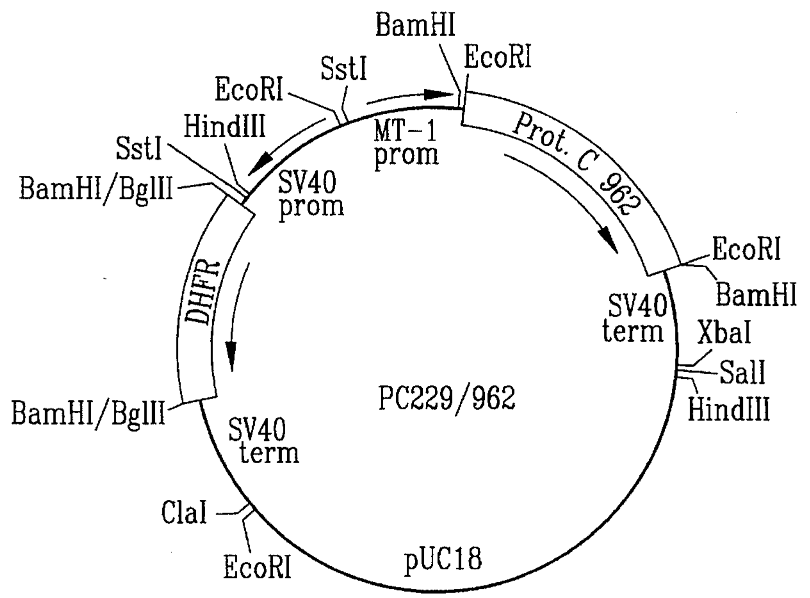
*Fig. 8*

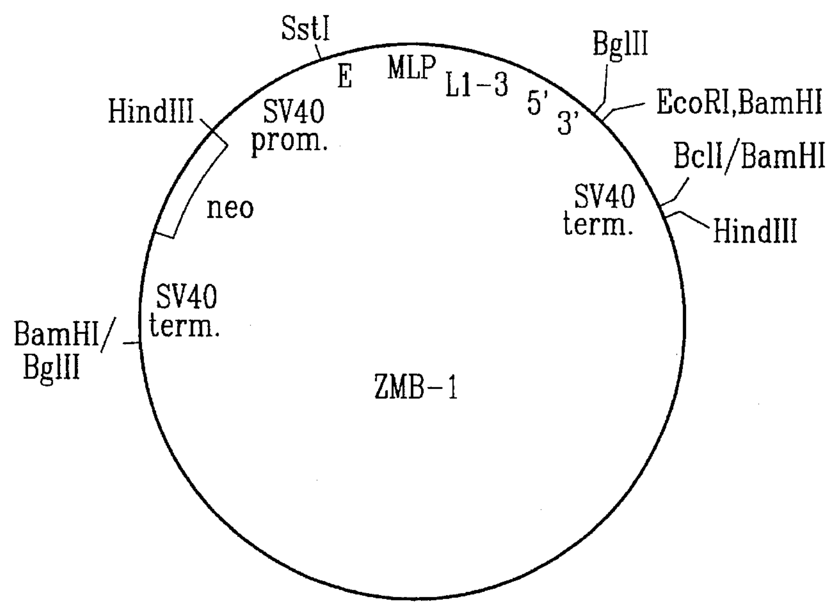
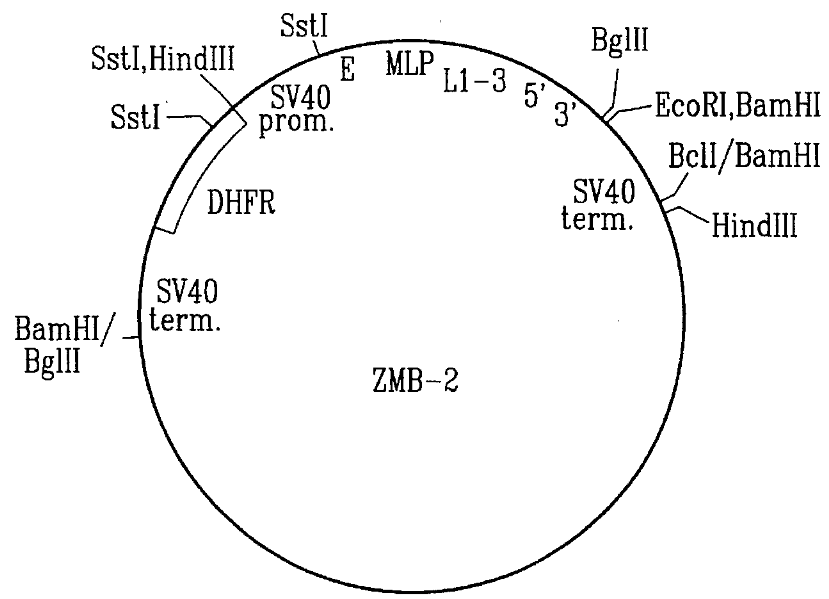
*Fig. 12*

PRODUCTION OF ACTIVATED PROTEIN C

This application is a continuation of U.S. patent application Ser. No. 07/987,532, filed Dec. 4, 1992, now abandoned, which is a continuation of U.S. Ser. No. 07/582,131, filed Sep. 10, 1990, now abandoned, which is a continuation of U.S. Ser. No. 07/317,205, filed Feb. 28, 1989, now abandoned, which is a continuation-in-part application of U.S. application Ser. No. 07/130,370, filed Dec. 8, 1987, now abandoned, which is a continuation-in-part of U.S. application Ser. No. 06/924,462, filed Oct. 29, 1986, which application issued as U.S. Pat. No. 4,959,318, which is a continuation-in-part of U.S. application Ser. No. 06/749,600, filed Jun. 27, 1985, which application is abandoned.

TECHNICAL FIELD

The present invention relates generally to plasma proteins and DNA sequences encoding those proteins, and more specifically to the expression of proteins having substantially the same biological activity as human protein C or human activated protein C.

BACKGROUND OF THE INVENTION

Protein C is a zymogen, or precursor, of a serine protease that plays an important role in the regulation of blood coagulation and in the generation of fibrinolytic activity in vivo. It is synthesized in the liver as a single-chain polypeptide that undergoes considerable processing to give rise to a two-chain molecule comprising heavy (Mr=40,000) and light (Mr=21,000) chains held together by a disulfide bond. The circulating two-chain intermediate is converted to the biologically active form of the molecule, known as "activated protein C" (APC), by the thrombin-mediated cleavage of a 12-residue peptide (also know as the activation peptide) from the amino-terminus of the heavy chain. The cleavage reaction is augmented in vivo by thrombomodulin, an endothelial cell co-factor (Esmon and Owen, *Proc. Natl. Acad. Sci. USA* 78:2249–2252, 1981).

Protein C is a vitamin K-dependent glycoprotein that contains approximately nine residues of gamma-carboxyglutamic acid (Gla) and one equivalent of beta-hydroxyaspartic acid, which are formed by post-translational modifications of glutamic acid and aspartic acid residues, respectively. The post-translational formation of specific gamma-carboxyglutamic acid residues in protein C requires vitamin K. These unusual amino acid residues bind to calcium ions and are believed to be responsible for the interaction of the protein with phospholipid, which is required for the biological activity of protein C.

In contrast to the coagulation-promoting action of other vitamin K-dependent plasma proteins, such as factor VII, factor IX, and factor X, activated protein C (APC) acts as a regulator of the coagulation process through the inactivation of factor Va and factor VIIIa by limited proteolysis. The inactivation of factors Va and VIIIa by protein C is dependent upon the presence of acidic phospholipids and calcium ions. Protein S has been reported to regulate this activity by accelerating the APC-catalyzed proteolysis of factor Va (Walker, *J. Biol. Chem.* 255:5521–5524, 1980).

Protein C has also been implicated in the action of tissue-type plasminogen activator (Kisiel and Fujikawa, *Behring Inst. Mitt.* 73:29–42, 1983). Infusion of bovine APC into dogs results in increased plasminogen activator activity (Comp and Esmon, *J. Clin. Invest.* 68:1221–1228, 1981). Other studies (Sakata et al., *Proc. Natl. Acad. Sci. USA* 82:1121–1125, 1985) have shown that addition of APC to cultured endothelial cells leads to a rapid, dose-dependent increase in fibrinolytic activity in the conditioned media, reflecting increases in the activity of both urokinase-related and tissue-type plasminogen activators. APC treatment also results in a dose-dependent decrease in anti-activator activity.

In some parts of the world, it is estimated that approximately 1 in 16,000 individuals exhibit protein C deficiency. Protein C deficiency is associated with recurrent thrombotic disease (Broekmans et al., *New Eng. J. Med.* 309:340–344, 1983 and Seligsohn et al., *New Eng. J. Med.* 310:559–562, 1984) and may result from genetic disorders or from trauma, such as injury, liver disease or surgery. Protein C deficiency is generally treated with oral anticoagulants. Beneficial effects have also been obtained through the infusion of protein C-containing normal plasma (see Gardiner and Griffin in Brown, Grune & Stratton, eds., *Prog. in Hematology,* 13:265–278, 1983, New York). In addition, protein C is useful in treating thrombotic disorders, such as venous thrombosis (Smith et al., PCT Publication No. WO 85/00521)

Activated protein C may be preferred over the zymogen for the treatment of thrombosis. The use of activated protein C bypasses the need for in vivo activation of protein C, thus providing a faster acting therapeutic agent.

Finally, exogenous activated protein C has been shown to prevent the coagulopathic and lethal effects of gram negative septicemia (Taylor et al., *J. Clin. Invest.* 79:918–925, 1987). Data obtained from studies with baboons suggest that activated protein C plays a natural role in protecting against septicemia.

While protein C may be purified from clotting factor concentrates (Marlar et al., *Blood* 59:1067–1072, 1982) or from plasma (Kisiel, *J. Clin. Invest.* 64:761–769, 1979) and activated in vitro, it is a complex and expensive process, in part due to the limited availability of the starting material and the low concentration of protein C in plasma. Furthermore, the therapeutic use of products derived from human blood carries the risk of disease transmission by, for example, hepatitis virus, cytomegalovirus, or human immunodeficiency virus (HIV). For these reasons, it is preferable to produce human protein C and human activated protein C by genetic engineering techniques. In view of the clinical applicability of human protein C and human activated protein C in the treatment of thrombotic disorders, the production of useful quantities of human protein C and human activated protein C by recombinant DNA techniques is clearly invaluable.

DISCLOSURE OF INVENTION

Briefly stated, the present invention discloses DNA sequences that code for proteins having substantially the same biological activity as human protein C or human activated protein C that have modifications which enhance the cleavage of the proteins between the light and heavy chains. In one aspect of the present invention, the DNA sequence further codes for the amino acid sequence $(R_1)_n$-$R_2$-$R_3$-$R_4$, wherein $R_1$, $R_2$, $R_3$ and $R_4$ are lysine (Lys) or arginine (Arg) and n is an integer between 0 and 3, between the light and heavy chains. In a preferred embodiment $(R_1)_n$-$R_2$-$R_3$-$R_4$ encodes the amino acid sequences Arg-Arg-Lys-Arg, Lys-Arg-Lys-Arg or Lys-Lys-Arg. In another aspect of the invention, the DNA sequence further codes for the amino acid sequence $R_1$-$R_2$-$R_3$-$R_4$-X-$R_5$-$R_6$-$R_7$-$R_8$, wherein $R_1$–$R_8$ are Lys or Arg and X is a peptide bond or a spacer peptide of 1 to 12 amino acids between the light and heavy chains. Preferred spacer peptides include Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln and Asp-Gln.

In another aspect of the invention a DNA sequence encoding protein C with native sequence or altered sequence as described above is co-expressed with the *Saccharomyces cerevisiae* KEX2 or KEX1 genes.

In yet another aspect of the present invention, a protein having substantially the same biological activity as human protein C or human activated protein C further includes the substitution of residue 158 (Asp) with a non-acidic amino acid residue such as Ala, Ser, Thr or Gly. In a related aspect, a protein having substantially the same biological activity as human protein C or human activated protein C further includes the substitution of residue 154 (His) with an amino acid residue such as Lys, Arg or Leu. In another aspect, a protein having substantially the same biological activity as human protein C or human activated protein C further includes the substitution of the Lys-Arg at residues 156–157 of native protein C with Lys-Lys or Arg-Arg.

Yet another aspect of the present invention is directed toward a DNA sequence that codes for a protein having substantially the same biological activity as human protein C or human activated protein C, the sequence further coding for the pre-pro peptide of a protein such as factor VII, factor IX, prothrombin or protein S.

In addition, the present invention discloses expression vectors capable of integration in mammalian host cell DNA, the vectors comprising a promoter operably linked to a DNA sequence, encoding a protein having substantially the same activity as human protein C or human activated protein C as set forth above, transcription of the nucleotide sequence being directed by the promoter. The nucleotide sequence is followed downstream by a polyadenylation signal. In one embodiment, the expression vector additionally contains a selectable marker driven by a second promoter.

A related aspect of the present invention discloses cultured mammalian cells transfected to express a protein having substantially the same biological activity as human protein C or human activated protein C. The cultured mammalian cells are transfected with an expression vector capable of integration into mammalian cell DNA, the expression vector including a promoter followed downstream by a DNA sequence as described above. Within one embodiment, a selectable marker driven by a second promoter is contained on the expression vector. Within another embodiment, a selectable marker is also introduced into the cells and stably transfected cells are selected. Preferred host cells for use within the present invention are COS-1, BHK and 293 cells. The cells may be further transfected with the KEX1 or KEX2 gene of *Saccharomyces cerevisiae*.

A further aspect of the invention discloses a method for producing a protein having substantially the same biological activity as human protein C or human activated protein C. The method comprises (a) introducing into a cultured mammalian host cell an expression vector comprising a DNA sequence as described above, which encodes a protein having substantially the same biological activity as human protein C or human activated protein C; (b) growing said cultured mammalian host cell in an appropriate growth medium; and (c) isolating the protein product encoded by said DNA sequence and produced by said cultured mammalian host cell. The protein produced according to this method is also disclosed.

The proteins described within the present invention may be used as active therapeutic substances, including use in the regulation of blood coagulation. Further, these protein may be combined with a physiologically acceptable carrier and/or diluent to provide suitable pharmaceutical compositions.

Other aspects of the invention will become evident upon reference to the following detailed description and attached drawings.

BRIEF DESCRIPTION OF THE DRAWINGS

FIG. 2 illustrates the nucleotide sequence of the complete protein C cDNA and the deduced amino acid sequence of protein C. Arrows indicate cleavage sites for removal of the connecting dipeptide and activation peptide.

FIG. 4 illustrates the complete genomic sequence, including exons and introns, of the human protein C gene. Arrowheads indicate intron-exon splice junctions. The polyadenylation or processing sequences of A-T-T-A-A-A and A-A-T-A-A-A at the 3' end are boxed. Filled diamonds indicate potential carbohydrate attachment sites; curved arrows indicate site of cleavage in the heavy chain when protein C is converted to activated protein C; filled circles indicate sites of polyadenylation.

FIG. 8 illustrates the expression vectors pDX/PC962 and PC962/229.

FIG. 12 illustrates the plasmids pZMB-1 and pZMB-2. Symbols are used as set forth in FIG. 6 and also include neo, neomycin resistance gene; SV40 term, SV40 terminator; SV40 prom, SV40 promoter

BEST MODE FOR CARRYING OUT THE INVENTION

Figure 1:
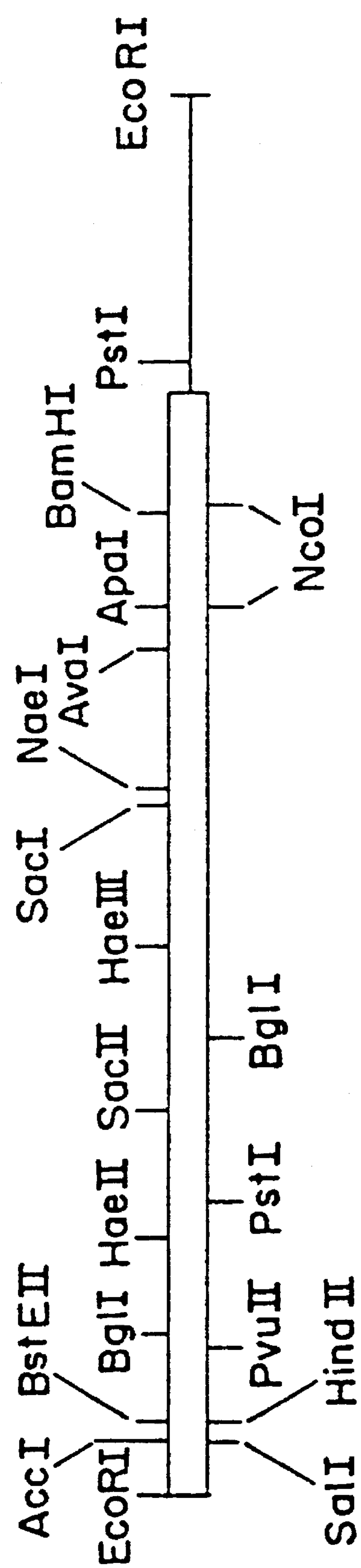
FIG. 1 is a partial restriction map of the protein C cDNA in pHCλ6L. The coding region is indicated by an open box.
Figure 3:
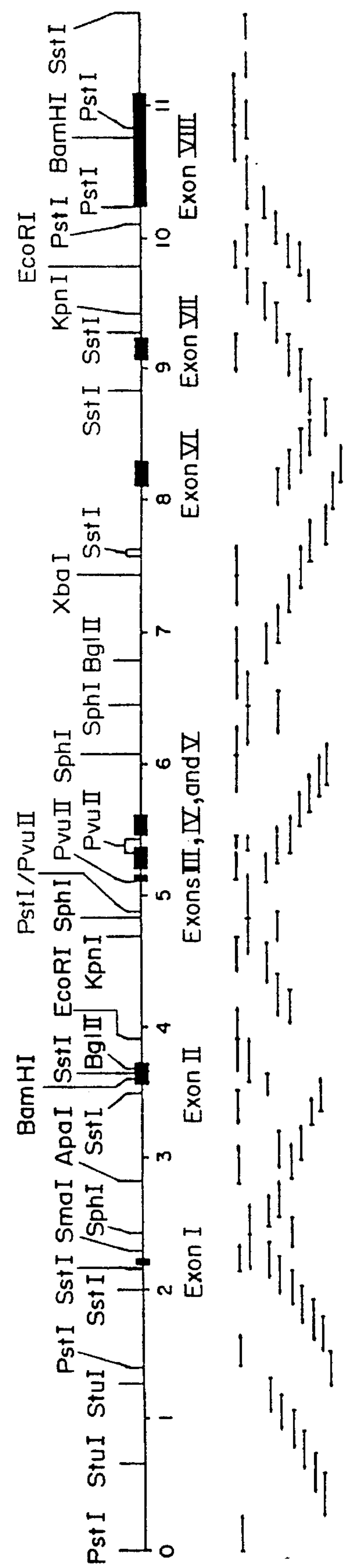
FIG. 3 illustrates a restriction enzyme map of the genomic DNA coding for human protein C. Numbers below the line indicate length in kilobases (kb).
Figure 5:
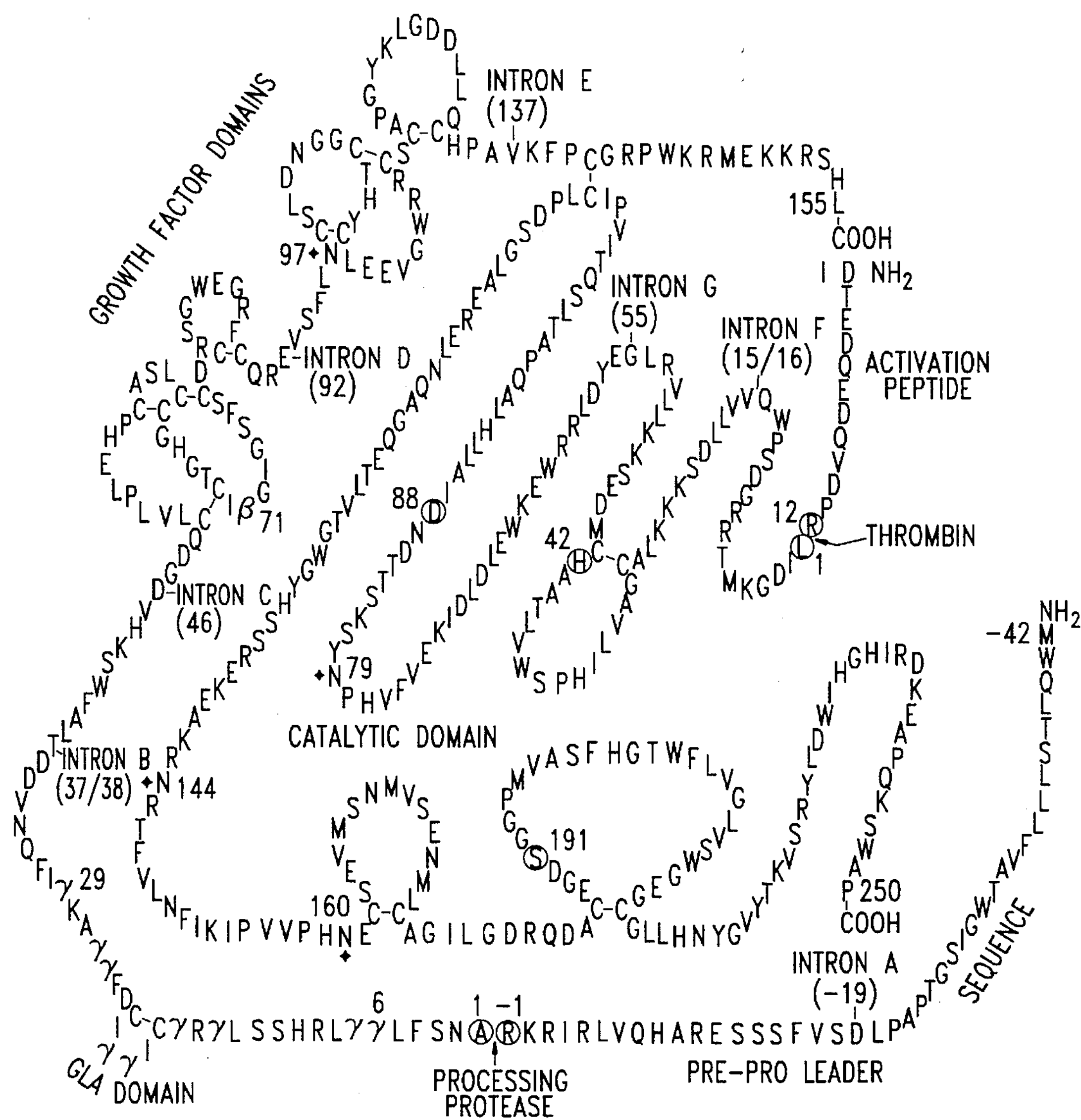
FIG. 5 illustrates a schematic two-dimensional model for the structure of human protein C.

Prior to setting forth the invention, it may be helpful to an understanding thereof to set forth definitions of certain terms to be used hereinafter.

Biological Activity: A function or set of functions performed by a molecule in a biological context (i.e., in an organism or an in vitro facsimile thereof). Biological activities of proteins may be divided into catalytic and effector activities. Catalytic activities of vitamin K-dependent plasma proteins generally involve specific proteolytic cleavages of other plasma proteins, resulting in activation or deactivation of the substrates. Effector activities include specific binding of the biologically active molecule to calcium, phospholipids or other small molecules, to macromolecules, such as proteins, or to cells. Effector activity frequently augments, or is essential to, catalytic activity under physiological conditions.

For activated protein C, biological activity is characterized by its anticoagulant and fibrinolytic properties. Activated protein C inactivates factor Va and factor VIIIa in the presence of acidic phospholipids and calcium. Protein S appears to be involved in the regulation of this function (Walker, ibid.). Activated protein C also enhances fibrinolysis, an effect believed to be mediated by the lowering of plasminogen activator inhibitors levels (van Hinsbergh et al., *Blood* 65:444–451, 1985). The catalytic activities of activated protein C reside in the heavy chain. A protein having substantially the same biological activity as protein C will be essentially free of this activity until activated.

Pre-Pro Peptide: An amino acid sequence that occurs at the amino terminus of some proteins and is generally cleaved from the protein during translocation. Pre-pro peptides comprise sequences directing the protein into the secretion pathway of the cell (signal sequences) and are characterized by the presence of a core of hydrophobic amino acids. Pre-Pro peptides may also comprise processing signals. As used herein, the term "pre-pro peptide" may also mean a portion of a naturally occurring pre-pro peptide.

Expression Vector: A DNA molecule which contains, inter alia, a DNA sequence encoding a protein of interest together with a promoter and other sequences that facilitate expression of the protein. Expression vectors further contain genetic information that provides for their replication in a host cell, either by autonomous replication or by integration into the host genome. Examples of expression vectors commonly used for recombinant DNA are plasmids and certain viruses, although they may contain elements of both. They also may include a selectable marker.

As noted above, protein C is produced in the liver and requires vitamin K for the formation of specific gamma-carboxyglutamic acid residues in the amino-terminal region of the light chain. These amino acid residues are formed by a post-translational modification and are required for calcium-mediated binding to phospholipid. In addition, protein C contains one beta-hydroxyaspartic acid residue that is also formed in a post-translational modification. However, the role of this amino acid residue is not known.

Protein C shows structural homology to other vitamin K-dependent plasma proteins, including prothrombin, factor VII, factor IX, and factor X. Similarities include the presence of the Gla residues in the light chain and the active site serine in the heavy chain, as well as other amino acid sequence homologies in the amino-terminal region of the light chain.

The present invention provides methods of producing a protein that is gamma-carboxylated and has the biological activity of human protein C or human activated protein C through the use of cultured mammalian cells transfected to stably express the protein. These methods rely in part on the use of novel cleavage sites to direct the cleavage of activated protein C and protein C precursors. These cleavage sites may be in the form of the amino acid sequence $(R_1)_n$-$R_2$-$R_3$-$R_4$, wherein $R_1$ through $R_4$ are lysine (Lys) or arginine (Arg) and n is an integer between 0 and 3, located between the light and heavy chains. Particularly preferred sequences include Arg-Arg-Lys-Arg, Lys-Arg-Lys-Arg and Lys-Lys-Arg. Alternatively, the cleavage sites may be of the form $R_1$-$R_2$-$R_3$-$R_4$-X-$R_5$-$R_6$-$R_7$-$R_8$, wherein $R_1$ through $R_8$ are Lys or Arg and X is a peptide bond or a spacer peptide of 1 to 12 amino acids between the light and heavy chains. Spacer peptides useful in this regard include the amino acid sequences Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln, Asp-Gln, and the native protein C activation peptide having the amino acid sequence Asp-Thr-Glu-Asp-Gln-Glu-Asp-Gln-Val-Asp-Pro-Arg. A third group of modifications that may increase the efficiency of cleavage include the substitution of amino acid residue 154 (His) of native protein C with an amino acid residue selected from the group consisting of Lys, Arg and Leu to give a processing site sequence of the general formula Y-Z-$R_1$-$R_2$, wherein Y is Lys, Arg or Leu; $R_1$ and $R_2$ are Lys or Arg; and Z is an amino acid other than Lys or Arg, preferably Leu. A fourth group of modifications includes substitution of the Asp residue at position 158 with a non-acidic amino acid residue. Use of a small neutral amino acid, such as Ala, Ser, Thr or Gly is preferred. A fifth group of modifications includes the substitution of Lys-Lys or Arg-Arg for the Lys-Arg of native protein C. Combinations of these groups of modifications may also be made. For example, a nonacidic amino acid may be substituted for the Asp residue at 158 in a protein C molecule containing a processing site having the sequence $(R_1)_n$-$R_2$-$R_3$-$R_4$. These modifications can be used in producing protein C or activated protein C.

The proteins of the present invention also include precursors of activated protein C, as well as variants and analogs of protein C and activated protein C containing the above-described cleavage sites. As used herein the light chain of protein C is understood to comprise amino acids 1–149 of the sequence disclosed in FIG. 1 or sequences substantially homologous thereto, or with C-terminal extensions. The heavy chain of protein C may or may not include the activation peptide. The heavy chain of activated protein C is understood not to include the activation peptide. Variants and analogs of protein C include those containing minor amino acid changes, such as those due to genetic polymorphism, and those in which blocks of amino acids have been added, deleted or replaced without substantially altering the biological activity of the proteins.

The present invention also provides a group of human protein C or human activated protein C analogs that have the protein C amino-terminal portion (gla domain) substituted with a gla domain of the vitamin-K dependent plasma proteins factor VII, factor IX, factor X, prothrombin or protein S. The amino-terminal portions of vitamin K-dependent plasma proteins are responsible for at least part of their respective calcium binding activities. It has been found that, as a result of this functional homology, the gla domains of these molecules may be interchanged and the resulting chimeric proteins still retain the activity specific to the catalytic domain. For example, as described in U.S. Pat. No. 4,789,950, the amino-terminal portion (calcium binding domain) of factor IX may be joined to factor VII at amino acid 38 to produce a protein having the activity of factor VII. Factor VII, factor IX, factor X, prothrombin, and protein S share this amino-terminal sequence homology with protein C. A cloned sequence comprising the 5'-coding region of the gene for any of these proteins may be substituted for the corresponding sequence of the protein C gene. Additionally, suitable coding sequences may be synthesized based on the known amino acid sequences of several of the vitamin K-dependent plasma proteins or on the sequence of protein C disclosed herein. Techniques for producing synthetic nucleotide sequences are well known in the art. For example, a set of overlapping oligonucleotides may be synthesized and annealed in pairs to yield double-stranded fragments with overlapping adhesive termini. These fragments are then ligated to form an adapter. The resultant synthetic adapter is then ligated using standard procedures for restriction fragments to the protein C or activated protein C cDNA at a convenient restriction site. The junction sequence may be modified as necessary by oligonucleotide-directed mutagenesis.

Cloned DNA sequences encoding protein C have been described (Foster and Davie, *Proc. Natl. Acad. Sci. USA* 81:4766–4770, 1984; Foster et al., *Proc. Natl. Acad. Sci. USA* 82:4673–4677, 1985 and Bang et al., U.S. Pat. No. 4,775,624). In general, cDNA sequences are preferred for carrying out the present invention due to their lack of intervening sequences which can lead to aberrant RNA processing and reduced expression levels. Complementary DNAs encoding protein C may be obtained from libraries prepared from liver cells according to standard laboratory procedures. It will be understood, however, that suitable DNA sequences can also be obtained from genomic clones or can be synthesized de novo according to conventional procedures. If partial clones are obtained, it is necessary to join them in proper reading frame to produce a full length clone, using such techniques as endonuclease cleavage, ligation, and loop-out mutagenesis.

The coding sequence will further encode a pre-pro peptide at the amino-terminus of the protein in order to obtain proper post-translational processing (e.g. gamma-carboxylation of glutamic acid residues) and secretion from the host cell. The pre-pro peptide may be that of protein C or another vitamin K-dependent plasma protein, such as factor VII, factor IX, factor X, prothrombin or protein S.

The cloned DNA sequence is then modified to include the cleavage sites of the present invention. Modification may be obtained by site-specific mutagenesis. Techniques of site-specific mutagenesis are well known in the art and are described by, for example, Zoller and Smith (*DNA* 3:479–488, 1984). Alternatively, the protein C sequence may be enzymatically cleaved to remove the native activation peptide sequence, and the sequences encoding the heavy and light chains joined to a synthesized activation peptide containing the cleavage sites.

To produce activated protein C (APC) directly, thereby removing the need to activate the protein product either in vitro or in vivo, a sequence encoding APC may be constructed by deleting the region encoding the activation peptide through oligonucleotide-directed deletion mutagenesis. Alternatively, novel cleavage sites may be introduced between the light chain and heavy chain or between the light chain and the activated heavy chain. The resultant protein will then be activated by cleavage and removal of the activation peptide and dibasic peptides during proteolytic processing in the secretion pathway of the host cell. It has been found that proteins lacking the activation peptide are nevertheless properly processed by the host cells, resulting in secretion of activated protein C.

The DNA sequence encoding a protein C or an activated protein C precursor is then inserted into a suitable expression vector, which is in turn used to transfect cultured mammalian cells. Expression vectors for use in carrying out the present invention will comprise a promoter capable of directing the transcription of a cloned gene or cDNA. Preferred promoters include viral promoters and cellular promoters. Viral promoters include the SV40 promoter (Subramani et al., *Mol. Cell. Biol.* 1:854–864, 1981) and the CMV promoter (Boshart et al., *Cell* 41:521–530, 1985). Cellular promoters include the mouse kappa gene promoter (Bergman et al., *Proc, Natl. Acad. Sci. USA* 81:7041–7045, 1983) and the mouse $V_H$ promoter (Loh et al., *Cell* 33:85–93, 1983). A particularly preferred viral promoter is the major late promoter from Adenovirus 2 (Kaufman and Sharp, *Mol. Cell. Biol.* 2:1304–13199, 1982). A particularly preferred cellular promoter is the metallothionein I promoter (Palmiter et al., *Science* 222:809–814, 1983). Such expression vectors may also contain a set of RNA splice sites located downstream from the promoter and upstream from the insertion site for the protein C sequence or within the protein C sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylations signal from SV40 (Kaufman and Sharp, ibid.), the polyadenylation signal from the adenovirus 5 Elb region or the human growth hormone gene terminator (DeNoto et al. *Nuc. Acids Res.* 9:3719–3730, 1981). The expression vectors may also include a noncoding viral leader sequence, such as the adenovirus 2 tripartite leader, located between the promoter and the RNA splice sites and enhancer sequences, such as the SV40 enhancer and the sequences encoding the adenovirus VA RNAs.

Cloned DNA sequences may then be introduced into cultured mammalian cells by, for example, calcium phosphate-mediated transfection (Wigler et al., *Cell* 14:725–732, 1978; Corsaro and Pearson, *Somatic Cell Genetics* 7:603–616, 1981; Graham and Van der Eb, *Virology* 52:456–467, 1973). Other techniques for introducing cloned DNA sequences into mammalian cells, such as electroporation (Neumann et al., *EMBO J.* 1:841–845, 1982), may also be used. In order to identify cells that have integrated the DNA, a gene that confers a selectable phenotype (a selectable marker) is generally introduced into the cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is the DHFR gene. A particularly preferred amplifiable marker is the $DHFR^r$ cDNA (Simonsen and Levinson, *Proc. Natl. Acad. Sci. USA* 80:2495–2499, 1983). Selectable markers are reviewed by Thilly (*Mammalian Cell Technology*, Butterworth Publishers, Stoneham, Mass.), and the choice of selectable markers is well within the level of ordinary skill in the art.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1–2 days, to begin expressing the gene of interest. As used herein the term "appropriate growth medium" means a medium containing nutrients required for the growth of cells. Nutrients required for cell growth may include a carbon source, a nitrogen source, vitamin K, essential amino acids, vitamins, minerals and growth factors. Drug selection is then applied to select for the growth of cells that are expressing the selectable marker in a stable fashion. For cells that have been transfected with an amplifiable selectable marker the drug concentration may be increased in a stepwise manner to select for an increased copy number of the cloned sequences, thereby increasing expression levels. Clones of stably transfected cells may be screened for expression of protein C or activated protein C.

Preferred cultured mammalian cells for use in the present invention include the COS-1 (ATCC CRL 1650), BHK and 293 (ATCC CRL 1573; Graham et al., *J. Gen. Virol.* 36:59–72, 1977) cell lines. A preferred BHK cell line is the $tk^-ts13$ BHK cell line (Waechter and Baserga, *Proc. Natl. Acad. Sci USA* 79:1106–1110, 1982). In addition, a number of other cell lines may be used within the present invention, including Rat Hep I (ATCC CRL 1600), Rat Hep II (ATCC CRL 1548), TCMK (ATCC CCL 139), Human lung (ATCC CCL 75.1), Human hepatoma (ATCC HTB-52), Hep G2 (ATCC HB 8065), NCTC 1469 (ATCC CCL 9.1) and DUKX cells (Urlaub and Chasin, *Proc. Natl. Acad. Sci. USA* 77:4216–4220, 1980).

Processing of human protein C or activated protein C precursors to the two-chain form may be enhanced by modifying the host cell. Processing of protein C by cleavage after a Lys-Arg dipeptide (e.g., amino acids 156–157 of the native sequence) and subsequent removal of these amino acids may be enhanced by introducing the *S. cerevisiae* KEX1 and/or KEX2 genes into the host cell. The KEX2 gene encodes an endopeptidase that cleaves after a dibasic amino acid sequence (Fuller et al., in Leive, ed., *MiCrobiology:* 1986, 273–278, 1986); the expression of the KEX1 gene (Dmochowska et al., *Cell* 50:573–584, 1987) results in the subsequent removal of these dibasic amino acids. A cultured mammalian cell line transfected with one or both of these genes is thus useful for expressing protein C or activated protein C. Co-expression of KEX2 is particularly useful in producing an activated protein C from an activated protein C precursor comprising a protein C sequence in which the activation peptide sequence has been removed and two basic amino acids have been inserted between the amino acid codons 155 and 156 of the native protein.

Human protein C or human activated protein C produced according to the present invention is preferably purified, as by affinity chromotography on an anti-protein C antibody column. The use of calcium-dependent monoclonal antibodies, as described by Wakabayashi et al. (*J. Biol. Chem.* 261:11097–11108, 1986), is particularly preferred. Additional purification of the column eluate may be achieved by conventional chemical purification means, such as high-performance liquid chromatography (HPLC).

Protein C produced according to the present invention may be activated by removal of the activation peptide from the amino terminus of the heavy chain. Activation may be achieved by incubating protein C in the presence of α-thrombin (Kiesel, ibid., 1979), trypsin (Marlar et al., *Blood* 59:1067–1072, 1982), Russell's viper venom factor X activator (Kisiel, et al., *Biochemistry* 15:4893–4900, 1976) or the commercially available venom-derived activator Protac C (American Diagnostica).

The protein C or activated protein C of the present invention may be used in pharmaceutical compositions for topical or intravenous application. The protein C or activated protein C is used in combination with a physiologically acceptable carrier or diluent. Preferred carriers and diluents include saline and sterile water. Pharmaceutical compositions may also contain stabilizers and adjuvants. The resulting aqueous solutions may be packaged for use or filtered under aseptic conditions and lyophilized, the lyophilized preparation being combined with a sterile aqueous solution prior to administration.

To summarize the examples which follow, Example 1 describes the cloning of cDNA and genomic DNA sequences encoding human protein C. Example 2 describes the expression of protein C in transfected mammalian cells. Example 3 describes the expression of protein C processing site mutants in mammalian cells. Example 4 describes the expression of activated protein C. Example 5 describes the use of the factor VII and prothrombin pre-pro peptides to secrete protein C.

The following examples are offered by way of illustration and not by way of limitation.

EXAMPLES

Restriction endonucleases and other DNA modification enzymes (e.g., T4 polynucleotide kinase, calf alkaline phosphatase, DNA polymerase I (Klenow fragment), T4 polynucleotide ligase) were obtained from Bethesda Research Laboratories (BRL) and New England Biolabs and were used as directed by the manufacturer, unless otherwise noted.

Oligonucleotides were synthesized on an Applied Biosystems Model 380A DNA synthesizer and purified by polyacrylamide gel electrophoresis on denaturing gels. *E. coli* cells were transformed as described by Maniatis et al. (*Molecular Cloning: A Laboratory Manual*, Cold Spring Harbor Laboratory, 1982). M13 and pUC cloning vectors and host strains were obtained from BRL.

EXAMPLE 1

Cloning of DNA Sequences Encoding Human Protein C

A cDNA coding for a portion of human protein C was prepared as described by Foster and Davie (ibid.). Briefly, a λgt11 cDNA library was prepared from human liver mRNA by conventional methods. Clones were screened using an $^{125}$I-labeled affinity-purified antibody to human protein C, and phage were prepared from positive clones by the plate lysate method (Maniatis et al., ibid.), followed by banding on a cesium chloride gradient. The cDNA inserts were removed using Eco RI and were subcloned into plasmid pUC9 (Vieira and Messing, *Gene* 19:259–268, 1982). Restriction fragments were subcloned in the phage vectors M13mp10 and M13mp11 (Messing, *Meth. in Enzymology* 101:20–77, 1983) and were sequenced by the dideoxy method (Sanger et al., *Proc. Natl. Acad. Sci. USA* 74:5463–5467, 1977). A clone was selected that contained DNA corresponding to the known partial sequence of human protein C (Kisiel, ibid., 1979) and encoded protein C beginning at amino acid 64 of the light chain and extending through the heavy chain and into the 3' non-coding region. This clone was designated λHC1375. A second cDNA clone coding for protein C from amino acid 24 was also identified. The insert from the larger clone was subcloned into pUC9 and the plasmid was designated pHCλ6L (FIG. 1). This clone encodes a major portion of protein C, including the heavy chain coding region, termination codon, and 3' non-coding region.

The cDNA insert from λHC1375 was nick translated using α-$^{32}$P dNTP's and used to probe a human genomic library in phage λCharon 4A (Maniatis et al., *Cell* 15:687–702, 1978) using the plaque hybridization procedure of Benton and Davis (*Science* 196:181–182, 1977) as modified by Woo (*Meth, Enzymol.* 68:381–395, 1979). Positive clones were isolated and plaque-purified (Foster et al., *Proc, Natl. Acad. Sci. USA* 82:4673–4677, 1985, herein incorporated by reference). Phage DNA prepared from positive clones (Silhavy et al., in *Experiments with Gene Fusion*, Cold Spring Harbor Laboratory, 1984) was digested with Eco RI or Bgl II and the genomic inserts were purified and subcloned in pUC9. Restriction fragments of the genomic inserts were subcloned into M13 vectors and sequenced to confirm their identity and establish the DNA sequence of the entire gene.

The cDNA insert of *pHCλ6L* was nick translated and used to probe the phage λCharon 4A library. One genomic clone was identified that hybridized to probes made from the 5' and 3' ends of the cDNA. This phage clone was digested with Eco RI, and a 4.4 kb fragment, corresponding to the 5' end of the protein C gene, was subcloned into pUC9. The resultant recombinant plasmid was designated pHCR4.4. Complete DNA sequence analysis revealed that the insert in pHCR4.4 comprised two exons of 70 and 167 base pairs separated by an intron of 1263 bp. The first exon encodes amino acids –42 to –19; the second encodes amino acids –19 to 37. Sequence analysis confirmed the DNA sequence of the entire protein C gene.

A genomic fragment containing an exon corresponding to amino acids –42 to –19 of the pre-pro peptide (Exon 1 in FIG. 4) of protein C was isolated, nick translated, and used as a probe to screen a cDNA library constructed by the technique of Gubler and Hoffman (*Gene* 25:263–269, 1983) using mRNA from Hep G2 cells. This cell line was derived from human hepatocytes and was previously shown to synthesize protein C (Fair and Bahnak, *Blood* 64:194–204, 1984). Ten positive clones comprising cDNA inserted into the Eco RI site of phage λgt11 were isolated and screened with an oligonucleotide probe corresponding to the 5' non-coding region of the protein C gene. One clone was also positive with this probe and its entire nucleotide sequence was determined. The cDNA contained 70 bp of 5' untranslated sequence, the entire coding sequence for human pre-pro-protein C, and the entire 3' non-coding region corresponding to the second polyadenylation site (FIG. 2).

EXAMPLE 2

Expression of Protein C

A. Construction of Vector pD3.

Figure 6:
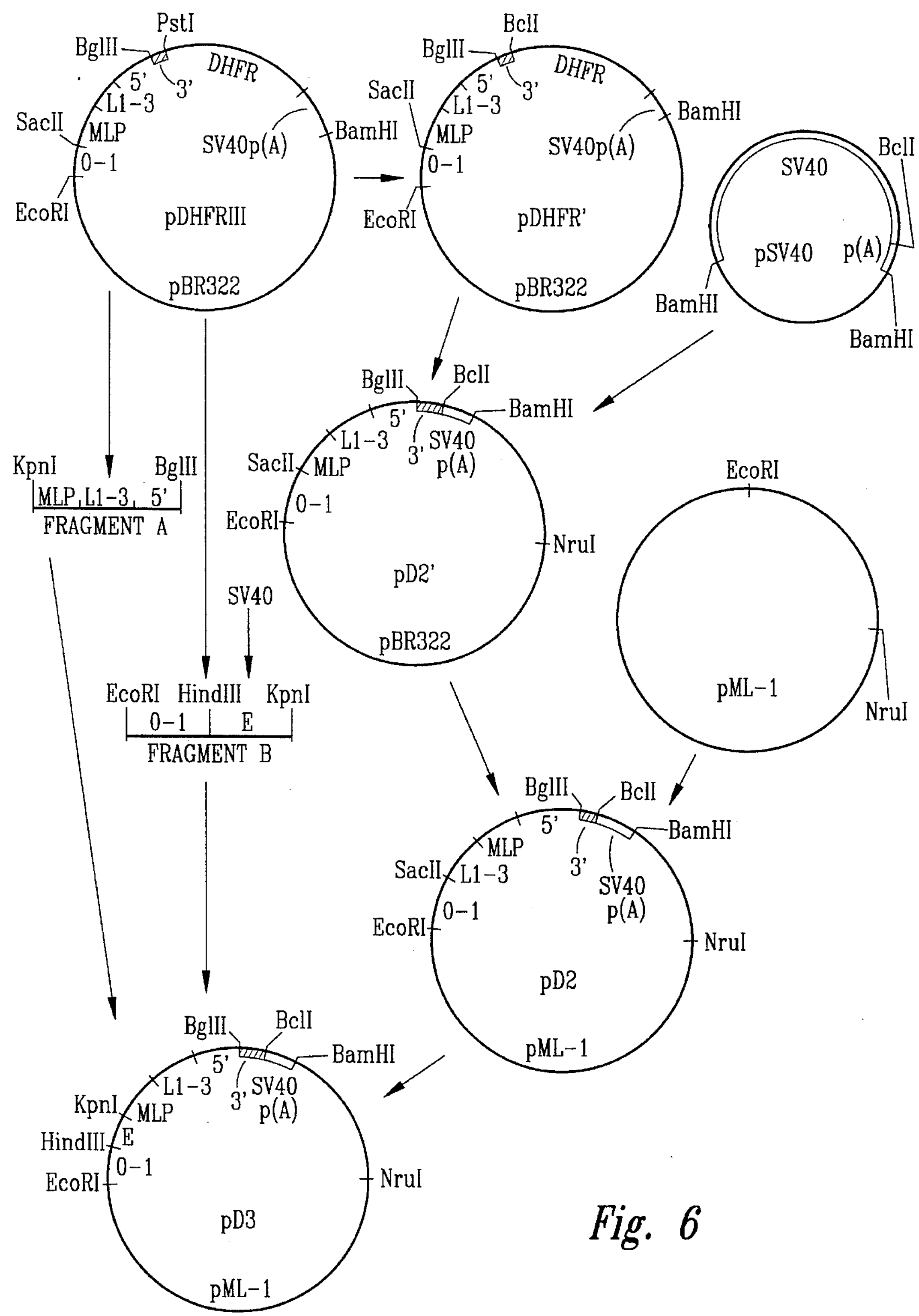
FIG. 6 illustrates the construction of the vector pD3. Symbols used are 0–1, the adenovirus 5 0–1 map unit sequence; E, the SV40 enhancer; MLP, the adenovirus 2 major late promoter; L1-3, the adenovirus 2 tripartite leader; 5', 5' splice site; 3', 3' splice site; p(A), polyadenylation signal; DHFR, dihydrofolate reductase gene.

The vector pD3 was derived from pDHFRIII (Berkner and Sharp, *Nuc. Acids Res.* 13:841–857, 1985) as shown in FIG. 6. The Pst I site immediately upstream from the DHFR sequence in pDHFRIII was converted to a Bcl I site by digesting 10 μg of plasmid with 5 units of Pst I for 10 minutes at 37° C. in 100 μl restriction buffer A (10 mM Tris pH 8, 10 mM $MgCl_2$, 6 mM NaCl, 7 mM β-MSH). The DNA was phenol extracted, ethanol precipitated, and resuspended in 40 μl polymerase buffer (50 mM Tris pH 8, 7 mM $MgCl_2$, 7 mM β-MSH) containing 10 mM dCTP and 16 units T4 DNA polymerase and incubated at 12° C. for 60 minutes. Following ethanol (EtOH) precipitation, the DNA was ligated to 2.5 μg kinased Bcl I linkers in 14 μl ligase buffer (10 mM Tris pH 8, 10 mM $MgCl_2$, 1 mM DTT, 1.4 mM ATP) containing 400 units T4 polynucleotide ligase for 12 hours at 12° C. Following phenol extraction and EtOH precipitation, the DNA was resuspended in 120 μl restriction buffer B (75 mM KCl, 6 mM Tris pH 7.5, 10 mM $MgCl_2$, 1 mM DTT), digested with 80 units Bcl I for 60 minutes at 50° C. then electrophoresed through agarose. Form III plasmid DNA (10 μg) was isolated from the gel, and ligated in 10 μl buffer C containing 50 units T4 polynucleotide ligase for 2 hours at 12° C., and used to transform *E. coli* HB101 Positive colonies were identified by rapid DNA preparation analysis, and plasmid DNA (designated pDHFR') prepared from positive colonies was transformed into dam$^-$ *E. coli.*

Plasmid pD2' was then generated by cleaving pDHFR' (15 μg) and pSV40 (comprising Bam HI digested SV40 DNA cloned into the Bam HI site of pML-1) (25 mg) in 100 μl restriction buffer B with 25 units Bcl I for 60 minutes at 50° C., followed by the addition of 50 units of Bam HI and additional incubation at 37° C. for 60 minutes. DNA fragments were resolved by agarose gel electrophoresis, and the 4.9 kb pDHFR' fragment and 0.2 kb SV40 fragment were isolated. These fragments (200 ng pDHFR' DNA and 100 ng SV40 DNA) were incubated in 10 μl ligase buffer containing 100 units T4 polynucleotide ligase for 4 hours at 12° C., and the resulting construct (pD2') was used to transform *E. coli* RR1.

Plasmid pD2' was modified by deleting the "poison" sequences in the pBR322 region (Lusky and Botchan, *Nature* 293:79–81, 1981). Plasmids pD2' (6.6 μg) and pML-1 (Lusky and Botchan, ibid.) (4 μg) were incubated in 50 μl restriction buffer A with 10 units each Eco RI and Nru I for 2 hours at 37° C., followed by agarose gel electrophoresis. The 1.7 kb pD2' fragment and 1.8 kb pML-1 fragment were isolated and ligated together (50 ng each) in 20 μl ligase buffer containing 100 units T4 polynucleotide ligase for 2 hours at 12° C., followed by transformation into *E. coli* HB101. Colonies containing the desired construct (designated pD2) were identified by rapid preparation analysis. Ten μg of pD2 was then digested with 20 units each Eco RI and Bgl II in 50 μl restriction buffer A for 2 hours at 37° C. The DNA was electrophoresed through agarose, and the desired 2.8 kb fragment, comprising the pML-1, 3' splice site and poly (A) sequences, was isolated.

To generate the remaining fragments used in constructing pD3, pDHFRIII was modified to convert the Sac II (Sst II) site into either a Hind III or Kpn I site. Ten μg pDHFRIII was digested with 20 units Sst II for 2 hours at 37° C., followed by phenol extraction and ethanol precipitation. Resuspended DNA was incubated in 100 μl polymerase buffer containing 10 mM dCTP and 16 units T4 DNA polymerase for 60 minutes at 12° C., phenol extracted, dialyzed, and ethanol precipitated. DNA (5 μg) was ligated with 50 ng kinased Hind III or Kpn I linkers in 20 μl buffer C containing 400 units T4 ligase for 10 hours at 12° C., phenol extracted, and ethanol precipitated. After resuspension in 50 μl restriction buffer A, the resultant plasmids were digested with 50 units Hind III or Kpn I, as appropriate, and electrophoresed through agarose. Gel-isolated DNA (250 ng) was ligated in 30 μl ligase buffer containing 400 units T4 DNA ligase for 4 hours at 12° C. and used to transform *E. coli* RR1. The resultant plasmids were designated pDHFRIII(Hind III) and pDHFRIII(Kpn I). A 700 bp Kpn I-Bgl II fragment was then purified from pDHFRIII(Kpn I) by digestion with Bgl II and Kpn I followed by agarose gel electrophoresis.

The SV40 enhancer sequence was inserted into pDHFRIII(Hind III) as follows: 50 μg SV40 DNA was incubated in 120 μl restriction buffer A with 50 units Hind III for 2 hours at 37° C., and the Hind III SV40 fragment (5089–968 bp) was gel purified. Plasmid pDHFRIII(Hind III) (10 μg) was treated with 250 ng calf intestinal phosphatase for 1 hour at 37° C., phenol extracted and ethanol precipitated. The linearized plasmid (50 ng) was ligated with 250 ng of the SV40-Hind III fragment in 16 μl ligase buffer for 3 hours at 12° C., using 200 units T4 polynucleotide ligase, and transformed into *E. coli* HB101. A 700 base pair Eco RI-Kpn I fragment was then isolated from this plasmid.

For the final construction of pD3,the 700 bp Kpn I-Bgl II fragment and the 700 bp Eco RI-Kpn I fragment (50 ng each) were ligated with 10 ng of the 2.8 kb pML-1, 3' splice site, poly(A) fragment with 200 units T4 polynucleotide ligase for 4 hours at 12° C., followed by transformation of *E. coli* RR1. Positive colonies were detected by rapid preparation analysis, and a large-scale preparation of pD3 (FIG. 6) was made.

B. Construction of Expression Vector p594.

The expression of protein C cDNA was achieved in the vector pDX. This vector was derived from pD3 and pD3', a vector identical to pD3 except that the SV40 polyadenylation signal (i.e., the SV40 Bam HI [2533 bp] to Bcl I [2770 bp] fragment) is in the late orientation. Thus, pD3' contains a Bam HI site as the site of gene insertion.

Figure 7:
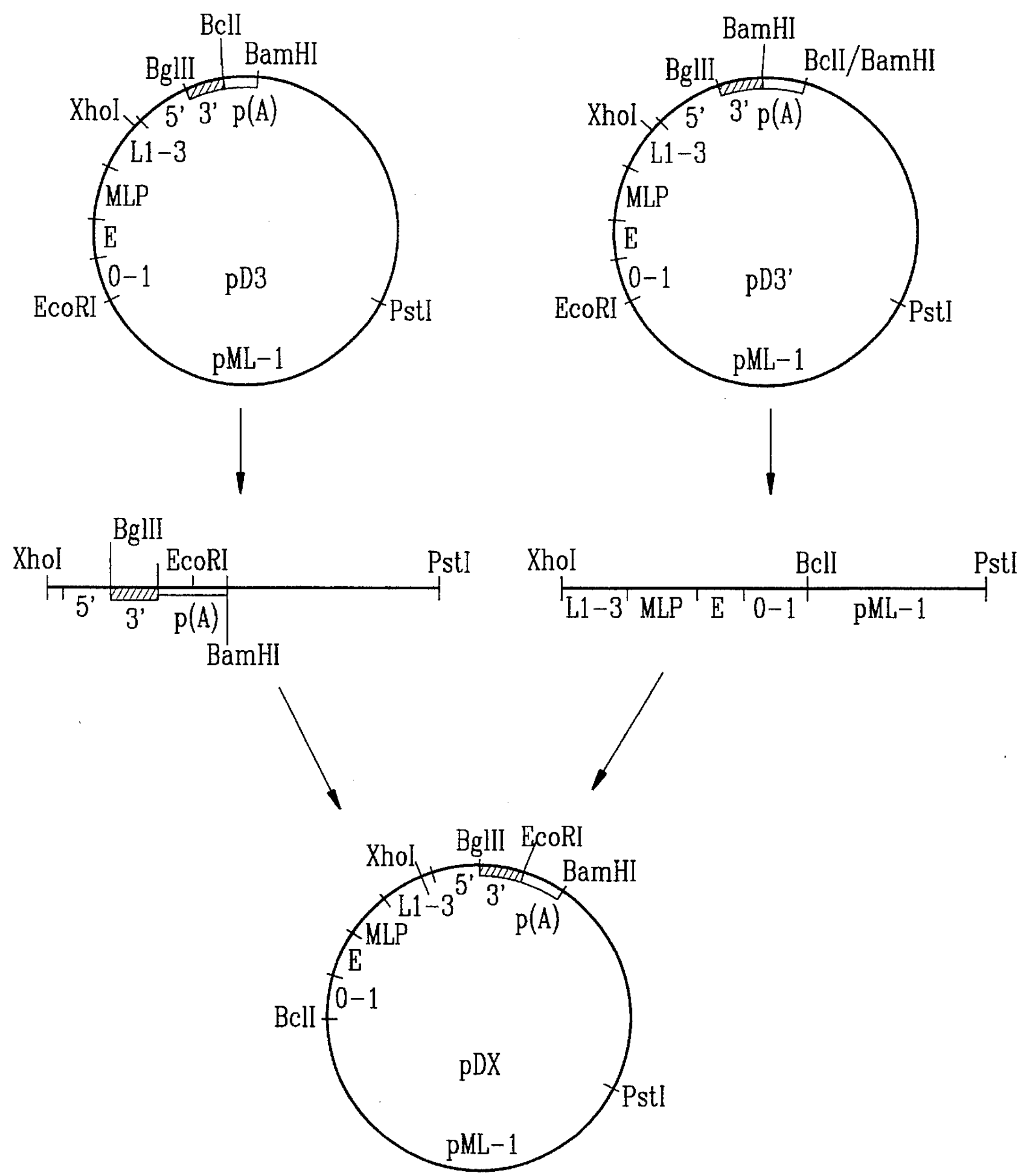
FIG. 7 illustrates the construction of the vector pDX. Symbols are used as set forth in FIG. 6.

To generate pDX, the Eco RI site in pD3' was converted to a Bcl I site by Eco RI cleavage, incubation with S1 nuclease, and subsequent ligation with Bcl I linkers. DNA was prepared from a positively identified colony, and the 1.9 kb Xho I-Pst I fragment containing the altered restriction site was prepared via agarose gel electrophoresis. In a second modification, Bcl I-cleaved pD3 was ligated with kinased Eco RI-Bcl I adapters (constructed from oligonucleotides ZC525, 5'GGA ATT CT 3'; and ZC526, 5'GAT CAG AAT TCC 3') in order to generate a unique Eco RI site for inserting a gene into the expression vector. A positive colony was identified by restriction endonuclease analysis, and DNA from this colony was used to isolate a 2.3 kb Xho I-Pst I fragment containing the modified restriction site. The two above-described DNA fragments were incubated together with T4 DNA ligase, transformed into *E. coli* HB101, and positive colonies were identified by restriction analysis. A preparation of such DNA, termed pDX (FIGS. 7), was then made. This plasmid contains a unique Eco RI site for insertion of foreign genes.

The protein C cDNA was then inserted into pDX as an Eco RI fragment. Recombinant plasmids were screened by restriction analysis to identify those having the protein C insert in the correct orientation with respect to the promoter elements, and plasmid DNA (designated pDX/PC) was prepared from a correct clone. Because the cDNA insert in pDX/PC contains an ATG codon in the 5' non-coding region (see FIG. 2), deletion mutagenesis was performed on the cDNA prior to transfection and expression experiments. Deletion of the three base pairs was performed according to standard procedures of oligonucleotide-directed mutagenesis. The pDX-based vector containing the modified cDNA was designated p594.

C. cDNA Expression.

Plasmid p594 was transfected into COS-1 (ATCC CRL 1650), $tk^-ts13$ BHK and 293 cells by calcium phosphate precipitation. Four hours later, fresh culture media (supplemented with 5 μg/ml vitamin K) were added. At appropriate times (usually 48 or 72 hours), the culture media were harvested and the cells were collected and lysed.

The protein C secreted into the culture media was assayed by enzyme-linked immunosorbent assay (ELISA) using the same affinity-purified polyclonal antibody, which was used in the initial identification of the cDNA clones, and/or a monoclonal antibody directed against the heavy chain of protein C. The affinity-purified antibody to human protein C (in 100 μg/ml in 0.1M $Na_2CO_3$, pH 9.6) was added to each well of 96-well microtiter plates, and the plates were incubated overnight at 4° C. The wells were washed three times with PBS (5 mM phosphate buffer, pH 7.5, 0.15M NaCl) containing 0.05% Tween-20 to remove unbound antibody and were incubated with 100 μl of 1% bovine serum albumin, 0.05% Tween 20 in PBS at 4° C. overnight. The plates were rinsed several times with PBS, air dried, and stored at 4° C. To assay samples, 100 μl of each sample was incubated for 1 hour at 37° C. in the coated wells, and the wells were rinsed with 0.05% Tween-20 in PBS. The plates were then incubated for 1 hour at 37° C. with a biotin-conjugated sheep polyclonal antibody to protein C (30 ng/ml) in PBS containing 1% bovine serum albumin and 0.05% Tween-20. The wells were rinsed with PBS and incubated for 1 hour at 37° C. with avidin-conjugated alkaline phosphatase in PBS containing 1% bovine serum albumin and 0.05% Tween-20. The wells were rinsed with PBS, and alkaline phosphatase activity was measured by the addition of 100 μl of phosphatase substrate (Sigma 104; 600 μg/ml in 10% diethanolamine, pH 9.8, containing 0.3 mM $MgCl_2$). The absorbance at 405 nm was read on a microtiter plate reader. Results of the assays of COS-1 and 293 cells are given in Table 1.

To assess the extent of gamma-carboxylation of the recombinant protein, samples of the culture media were subjected to barium citrate precipitation, a process which selectively precipitates only gamma-carboxylated proteins from plasma (Bajaj et al., *J. Biol. Chem.* 256: 253–259, 1981). Over 70% of the protein C antigenic material could be precipitated with barium citrate.

The recombinant protein C was assayed for anticoagulant activity by measuring its ability to prolong coagulation. Dialyzed media samples were treated with Protac C (American Diagnostica) to activate the protein C. The activated samples were then added to an in vitro clotting assay (Sugo et al., *J. Biol. Chem.* 260:10453, 1985). Briefly, 50 μl each of normal pooled human plasma, rabbit brain cephalin (10 mg/ml in TBS [50 mM Tris pH 7.5, 150 mM NaCl]) and kaolin suspension (5 mg/ml in TBS) were mixed in a siliconized glass tube. After preincubation at 37° C. for 2 minutes, 100 μl of activated protein C sample diluted in TBS was added and the 37° C. incubation was continued for an additional 2 minutes. Clotting was then initiated by the addition of 50 μl of 25 mM $CaCl_2$, and the clotting time was recorded. The activity of the recombinant material was shown to be essentially the same as that of plasma protein C.

Protein C produced by transfected $tk^-ts13$ BHK and 293 cells was further analyzed by Western blotting. Media samples were electrophoresed on denaturing gels, and blots were prepared and probed with radiolabeled antibody to protein C. Results indicated that about 20% of the protein C from BHK cells was in the two-chain form, while about 90% of that from 293 cells was processed to the two-chain form.

TABLE 1

TRANSIENT EXPRESSION AND SECRETION OF PROTEIN C IN COS-1 AND 293 CELLS

| Cells | Plasmid | ng/ml Protein C In Media |
|---|---|---|
| COS-1 | none | 0 |
| COS-1 | p594 | 10 |
| 293 | none | 0 |
| 293 | p594 | 50 |

EXAMPLE 3

Modification of the Protein C Processing Site

A. Site Specific Mutagenesis.

To enhance the processing of single-chain protein C to the two-chain form, two additional arginine residues were introduced into the protein, resulting in a cleavage site consisting of four basic amino acids. The resultant mutant precursor of protein C, designated PC962, contains the sequence Ser-His-Leu-Arg-Arg-Lys-Arg-Asp at the cleavage sits (Table 2; the amino acids that have been added to the sequence encoding wild-type (594) protein C appear in bold and spaces between amino acids are used solely for aligning the light and heavy chain sequences). Processing at the Arg-Asp bond results in a two-chain protein C molecule.

TABLE 2

Amino Acid Sequences of Cleavage-Site Mutants

| Mutant | 149 | 155 | | 170 |
|---|---|---|---|---|
| 594WT | E—K | —K—R—S—H—L— | K—R—D—T—E—D—Q—E—D—Q—V—D—P—R— | L—I—D— |
| 829 | E—K— | K—R—S—H—L— | K—R— | L—I—D— |
| 962 | E—K— | K—R—S—H—L—R—R—K—R—D—T—E—D—Q—E—D—Q—V—D—P—R— | | L—I—D— |
| 1058 | E—K— | K—R—S—H—L—R—R—K—R— | | L—I—D— |
| 1645 | E—K— | K—R—S—H—L—R—R—K—R—D—T—E—D—Q—E—D—Q—R—R—K—R— | | L—I—D— |
| 1880 | E—K— | K—R—S—H—L—R—R—K—R—D—T— | D—Q—R—R—K—R— | L—I—D— |
| 1953 | E—K— | K—R—S—H—L—R—R—K—R— | R—R—R—R— | L—I—D— |
| 1954 | E—K— | K—R—S—H—L—R—R—K—R—D— | Q—R—R—K—R— | L—I—D— |
| 1962 | E—K— | K—R— | | L—I—D— |
| 2043 | E—K—R—K—R— | | | L—I—D— |

The mutant molecule was generated by altering the cloned cDNA by site-specific mutagenesis (essentially as described by Zoller and Smith, *DNA* 3:479–488, 1984) using the mutagenic oligonucleotide ZC962 (5' AGT CAC CTG AGA AGA AAA CGA GAC A 3') and oligonucleotide ZC550 (5' TCC CAG TCA CGA CGT 3'). Plasmid p594 was digested with Sst I, the approximately 87 bp fragment was cloned into M13mp11, and single-stranded template DNA was isolated. Following mutagenesis, a correct clone was identified by sequencing. Replicative form DNA was isolated and was digested with Sst I to isolate the mutagenized fragment. This mutagenized fragment was joined with Sst I-cut p594 in a two-part ligation. Clones having the Sst I fragment inserted in the desired orientation were identified by restriction enzyme mapping. The resulting expression vector was designated pDX/PC962 (FIG. 8).

B. Expression and Characterization of Protein C.

Plasmid pDX/PC962 was co-transfected into $tk^{-}ts13$ BHK cells with pSV2-DHFR (Subramani et al., *Mol. Cell. Biol.* 1:854–864, 1981) by the calcium phosphate procedure (essentially as described by Graham and van der Eb, ibid.). The transfected cells were grown in Dulbecco's modified Eagle's medium (DMEM) containing 10% fetal calf serum, 1× PSN antibiotic mix (Gibco 600–5640), 2.0 mM L-glutamine and vitamin K (5 μg/ml). The cells were selected in 250 nM methotrexate (MTX) for 14 days, and the resulting colonies were screened by the immunofilter assay (McCracken and Brown, *BioTechniques,* 82–87, March/April 1984). Plates were rinsed with PBS or No Serum medium (DMEM plus 1× PSN antibiotic mix, 5 μg/ml vitamin K). Teflon® mesh (Spectrum Medical Industries, Los Angeles, Calif.) was then placed over the cells. Nitrocellulose filters were wetted with PBS or No Serum medium, as appropriate, and placed over the mesh After a four hour incubation at 37° C., the filters were removed and placed in filter buffer (50 mM Tris pH 7.4, 5 mM EDTA, 0.05% NP-40, 150 mM NaCl, 0.25% gelatin) for 30 minutes at room temperature. The filters were incubated for 1 hour at room temperature, with shaking, in biotin-labeled sheep anti-protein C polyclonal antibody (1 μg/ml in filter buffer). Filters were then washed in the same buffer and incubated 1 hour at room temperature, with shaking, in avidin-conjugated horseradish peroxidase (Boehringer-Mannheim) (diluted 1:1000 in the filter buffer). Filters were washed in 50 mM Tris-HCl, pH 7.4, 5 mM EDTA, 1M NaCl, 0.25% gelatin, 0.4% sacrosyl, 0.05% NP-40, then in $H_2O$. The washed filters were incubated in color reagent (60 mg HRP color development reagent [Bio-Rad], 20 ml methanol, 100 μl $H_2O_2$ in 100 ml 50 mM Tris pH 7.4, 150 mM NaCl). The reaction was stopped by transferring the filters to $H_2O$. Six of the most intensely reacting colonies were picked by cylinder cloning and were grown individually in 10 cm plates. When the cultures were nearly confluent, protein C production levels were measured by ELISA. Results are given in Table 3.

TABLE 3

| Clone | Cell No. ($\times 10^{-7}$) | ELISA ng/ml | pg/cell/day |
|---|---|---|---|
| 962-1 | 1.1 | 2500 | 2.20 |
| -2 | 0.8 | 1250 | 1.56 |
| -3 | 1.2 | 1350 | 1.12 |
| -4 | 1.2 | 550 | 0.46 |
| -5 | 1.2 | 1550 | 1.30 |
| -6 | 1.2 | 950 | 0.80 |

The clone BHK/962-1 was grown in larger scale culture, and several hundred micrograms of protein C was purified by affinity chromatography on a column prepared by coupling 7 mg of polyclonal sheep antibody against human protein C to 2 grams of CNBr-activated Sepharose 4B (Pharmacia Inc., Piscataway, N.J.). Cell culture medium was applied to the column and the column was washed with 100 ml TBS. The protein C was eluted with TBS containing 3M KSCN or with pH 11.5 buffer (25 mM potassium phosphate, pH 11.5, 0.2M NaCl, 2% Tween-80, 0.5% $NaN_3$). Western blot analysis demonstrated that the mutant protein C was approximately 95% in the two-chain form, compared to about 20% two-chain protein C obtained from tk⁻ts13 BHK cells transfected with the native sequence.

The BHK-produced PC962 protein was assayed for its ability to be activated to a form that shows both amidolytic and anticoagulant activities. Affinity-purified protein samples were exhaustively dialyzed against TBS, then activated by incubation at 37° C. for 1 hour with 0.1 volume of 1 unit/ml Protac C (American Diagnostica). Amidolytic activity was measured by adding aliquots of the activation mixture to 100 μl of 1 mM protein C substrate (Spectrozyme PCa, American Diagnostica) in a microtiter well and measuring the change in $A_{405}$ over time using a microtiter plate reader. Anticoagulant activity of the activated protein C was assayed as described by Sugo et al. (ibid.). The affinity-purified PC962 protein was demonstrated to be fully active in both amidolytic and anticoagulant assays. Elution from the antibody column with pH 11.5 buffer was shown to yield a protein with higher activity than that obtained using 3M KSCN elution.

Milligram quantities of protein C were purified from either stable tk⁻ts13 BHK cell clones expressing the PC962 mutant protein or stable 293 cell clones expressing the wild-type protein C (p594 transfected cells) using a monoclonal antibody column specific for the calcium-induced conformation of protein C. Cell culture media were applied to the column in the presence of 5 mM $CaCl_2$, and protein C was eluted from the column with TBS containing 10 mM EDTA. The use of this purification method permitted purification of completely active protein C without exposure to denaturing conditions. The purified protein C was analyzed by SDS/PAGE followed by silver staining and was shown to be >95% pure.

Clonal cell lines from the pDX/PC962 transfection into tk⁻ts13 BHK cells were isolated by a process of limiting dilution. One plate of MTX-selected colonies (approximately 300 colonies) was trypsinized, counted, and re-plated into microtiter wells at an average of 0.5 cell/well. These were grown up in selective media containing 250 nM MTX. About 50% of the wells contained colonies. Wells containing identifiable colonies (1–2 mm diameter) were assayed by ELISA for protein C level in the media. For this assay, fresh medium was added to all the wells, allowed to incubate for 75 minutes, then removed and assayed. Five colonies which gave 75-minute accumulations of greater than 50 ng/ml (corresponding to over 1000 ng/ml/day) were split into 10-cm plates for larger scale culture. Protein C production levels for these clones ranged from 1.1 to 2.8 pg/cell/day.

A second plasmid, designated PC229/962, was constructed by inserting the PC962 cDNA into plasmid Zem229. Zem229 is a pUC18-based expression vector containing a unique Bam HI site for insertion of foreign DNA between the mouse metallothionein-I promoter and SV40 transcription terminator. Zem229 also contains an expression unit comprising the SV40 early promoter, mouse dihydrofolate reductase gene, and SV40 terminator. An Eco RI fragment containing the PC962 cDNA from pDX/PC962 was ligated, with Eco RI-Bam HI oligonucleotide adapters, to Zem229, which had been cut with Bam HI and treated with phosphatase. The resulting vector is PC229/962, illustrated in FIG. 8.

Plasmid PC229/962 was transfected into tk⁻ts13 BHK cells by the calcium phosphate method. Cells were cultured in DMEM containing 5% fetal calf serum and 5 μg/ml vitamin K. The 48-hour transient expression level from this transfection was approximately 25 ng/ml. After 2 days, the transfected cells were split into selective media containing 1 μM MTX and cultured for an additional 14 days. Three plates from this transfection, containing approximately 200 colonies each, were screened by the immunofilter assay, and the 24 most intensely reacting colonies were picked by cylinder cloning. The twenty-four colonies were grown individually in 10-cm plates, and their protein C production levels were measured. Colonies producing between 1.1 and 2.3 pg/cell/day were used for the production of stable protein C-producing cell lines.

Expression vector pDX/PC962 and plasmid pKO-neo were co-transfected by the calcium phosphate method into 293 cells. pKO-neo comprises the SV40 early promoter operatively linked to the neomycin resistance gene followed downstream by the SV40 small t poly(A) sequence and plasmid pKO-1 vector sequences. Transfected cells were split into media containing 500 μg/ml G418 after 48 hours. After 10 days in selective media, immunofilter assays were done, and two clones were picked by cylinder cloning. Protein C production was found to range from 1 to 2 pg/cell/day. The cultures were scaled up, and protein C was purified by immuno-affinity chromatography. Greater than 95% of the protein C was found to be in the two-chain form.

The structure of the PC962 mutant protein prepared from tk⁻ts13 BHK and 293 cells was compared to that of wild-type protein C from 293 cells and from plasma. Analysis by SDS/PAGE followed by silver staining showed that all the recombinant proteins contained heavy and light chains which co-migrated with those of the plasma protein. The wild-type protein C synthesized in 293 cells contained a significant amount (approximately 20%) of single-chain, unprocessed protein of Mr=66,000, whereas the mutant protein produced in either cell type was essentially completely processed to two chains. N-terminal sequence analysis showed that both the light and heavy chains of the recombinant wild-type and BHK/PC962 mutant proteins were properly processed. The extent of gamma-carboxylation of the recombinant proteins was measured by two distinct ELISA systems. The first system recognizes both gamma-carboxylated and non-carboxylated forms of the protein, while the second utilizes specific antibodies that only recognize protein C that has undergone a gla-induced conformational change in the presence of calcium. Analysis indicated that approximately 60% of the recombinant protein C produced in tk⁻ts13 BHK cells and 90%–95% of that produced in 293 cells was sufficiently gamma-carboxylated to be recognized by the specific antibodies.

The three recombinant proteins were also analyzed for amidolytic and anticoagulant activities and the results were compared to the activity of plasma protein C. PC962 from tk⁻ts13 BHK cells and wild-type protein C from 293 cells both showed full amidolytic activity. In the anticoagulant assay, protein C from tk⁻ts13 BHK cells and 293 cells had essentially the same specific activity as plasma protein C. One unit of protein C activity is defined as the amount in 1 ml of normal human plasma, which contains 4 μg of protein C per 1 ml (Gardiner and Griffin, *Prog. Hematol.* 13:265–278, 1983) (specific activity=250 units/mg).

EXAMPLE 4

Expression of Activated Protein C

A. Construction and Expression of pPc829.

The cDNA sequence encoding protein C was altered by site-specific mutagenesis to delete the portion encoding the activation peptide. The amino acid sequence of the junction between the light and heavy chains of the protein C mutant, designated 829, is shown in Table 2. The altered sequence was then transfected into tk⁻ts13 BHK and 293 cells, and stably transfected cells were selected. Active protein C was detected in culture media samples from both cell lines.

To delete the activation peptide coding sequence, plasmid p594 was digested with Sst I, and the ~880 bp fragment was purified and inserted into the Sst-I site of M13mp10 (Messing, *Meth. Enzymol.* 101:20–77, 1983). The 12 activation peptide codons were deleted by oligonucleotide-directed deletion mutagenesis (Zoller and Smith, *DNA* 3:479–488, 1984) using the mutagenic oligonucleotide ZC829 (5' CTG AAA CGA CTC ATT GAT 3'). Replicative form DNA was prepared from mutant phage clones and digested with Sst I. The protein C fragment (~840 bp) was isolated and inserted into Sst I-digested p594. The resultant plasmids were screened for proper orientation of the Sst I fragment by restriction mapping using Bgl II. A correct plasmid was selected and designated pPC829. Plasmid pPC829 was sequenced to verify the presence of the desired coding sequence.

Plasmid pPC829 was co-transfected into $tk^{-}$ts13 BHK cells (with plasmid pSVDHFRT (Lee et al., *Nature* 294:228–232, 1982)) and 293 cells (with pKO-neo) by calcium phosphate coprecipitation (Graham and van der Eb, *Virology* 52:456–467, 1973). After 48 hours, culture media were harvested and assayed for protein C by ELISA. Results are shown in Table 4. At the same time, cultures were split 1:5 into media containing 500 μg/ml of G418 (293 cells) or 250 nM methotrexate ($tk^{-}$ts13 BHK cells). After being grown 10 days in the presence of selective media, stably transfected colonies were screened for protein C production by immunofilter assay.

Figure 9:
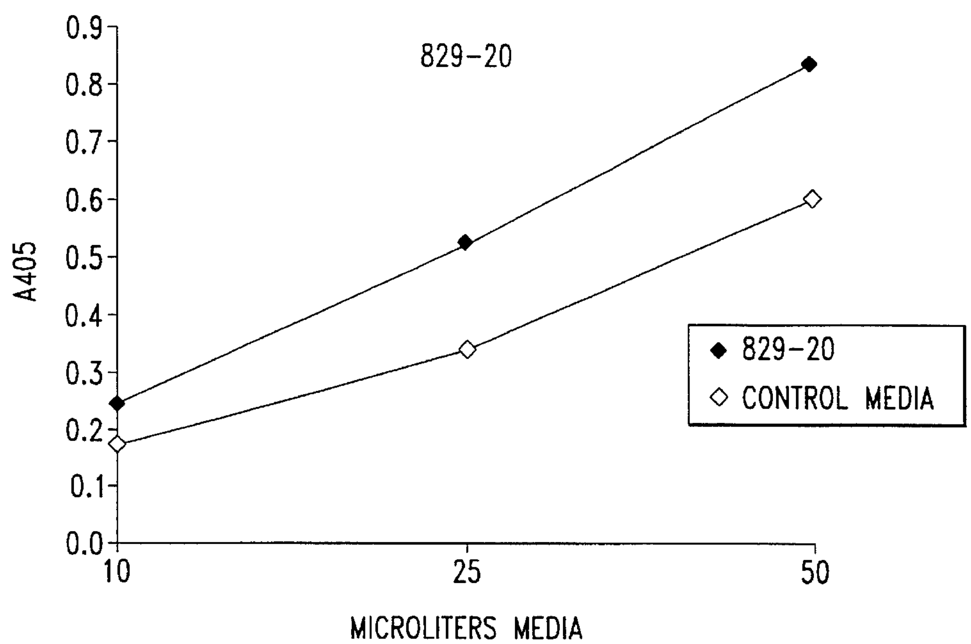
FIG. 9 illustrates the results of an assay for activated protein C on media samples from transfected 293 cells.

Positive colonies were picked and grown in selective media (containing 500 μg/ml G418 or 250 nM methotrexate, as appropriate) for 10 days. Culture media were assayed for APC activity by chromogenic assay. Media samples were added to microtiter wells containing 100 μl of 0.2 mM Spectrozyme PCa (American Diagnostica #336) in 50 mM Tris pH 7.5, 150 mM NaCl. Plates were incubated at 37° C., and the $A_{405}$ was measured at various time intervals. Representative results from one transfected 293 cell line (designated 829–20) are shown in FIG. 9. Media from positive colonies of line 829–20 consistently showed higher activity with the chromogenic substrate for APC than did control media which had been incubated with non-transfected 293 cells for the same length of time (10 days).

TABLE 4

TRANSIENT EXPRESSION OF ACTIVATED PROTEIN C (ELISA)

| Cell Line | Protein C ng/ml in Media |
|---|---|
| $tk^{-}$ts13 BHK | 2.7 |
| 293 | 30 |

B. Construction and Expression of DDX/Pc1058.

A DNA sequence encoding an activated protein C precursor with the cleavage site sequence Arg-Arg-Lys-Arg was constructed by mutagenesis of the wild-type protein C sequence. The resultant sequence (designated 1058) was analogous to that encoding PC962, but lacked the portion encoding the activation peptide. The amino acid sequence at the junction between the light and heavy chains is presented in Table 2.

The protein C sequence present in plasmid p594 was altered in a single mutagenesis to delete the codons for the activation peptide and insert the Arg-Arg codons at the processing site. A mutagenesis was performed on the 870 bp Sst I fragment from p594 essentially as described in Example 3.A. using oligonucleotides ZC1058 (5' CGC AGT CAC CTG AGA AGA AAA CGA CTC ATT GAT GGG 3') and ZC550.

The mutagenized sequence was used to construct expression vector pDX/PC1058 (analogous to pDX/PC962), and the vector was co-transfected into $tk^{-}$ts13 BHK cells as described in Example 3.B. The protein was purified on a polyclonal antibody column eluted with pH 11.5 buffer.

Figure 10:
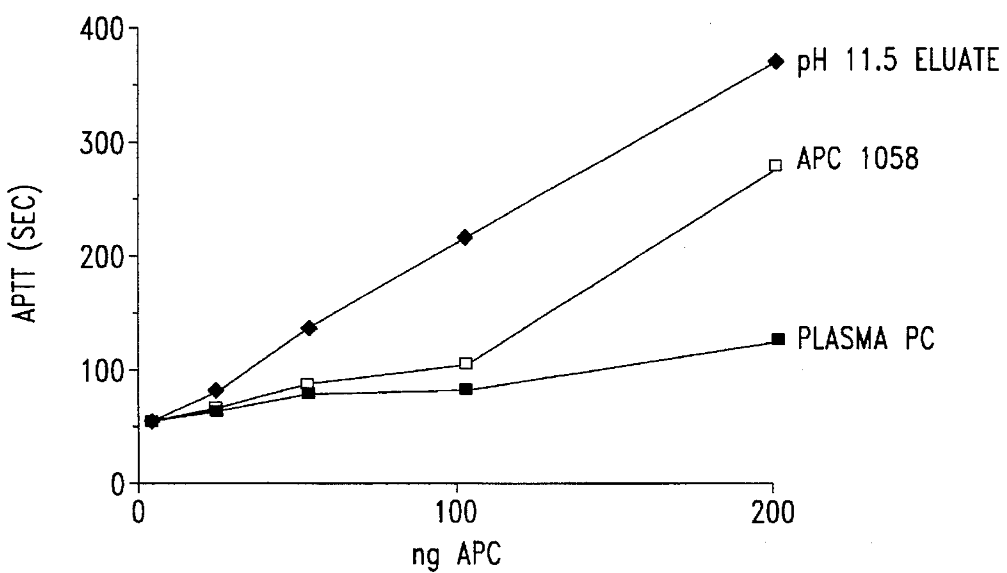
FIG. 10 illustrates the anticoagulant activity of protein C prepared according to certain embodiments of the present invention.
Figure 11:
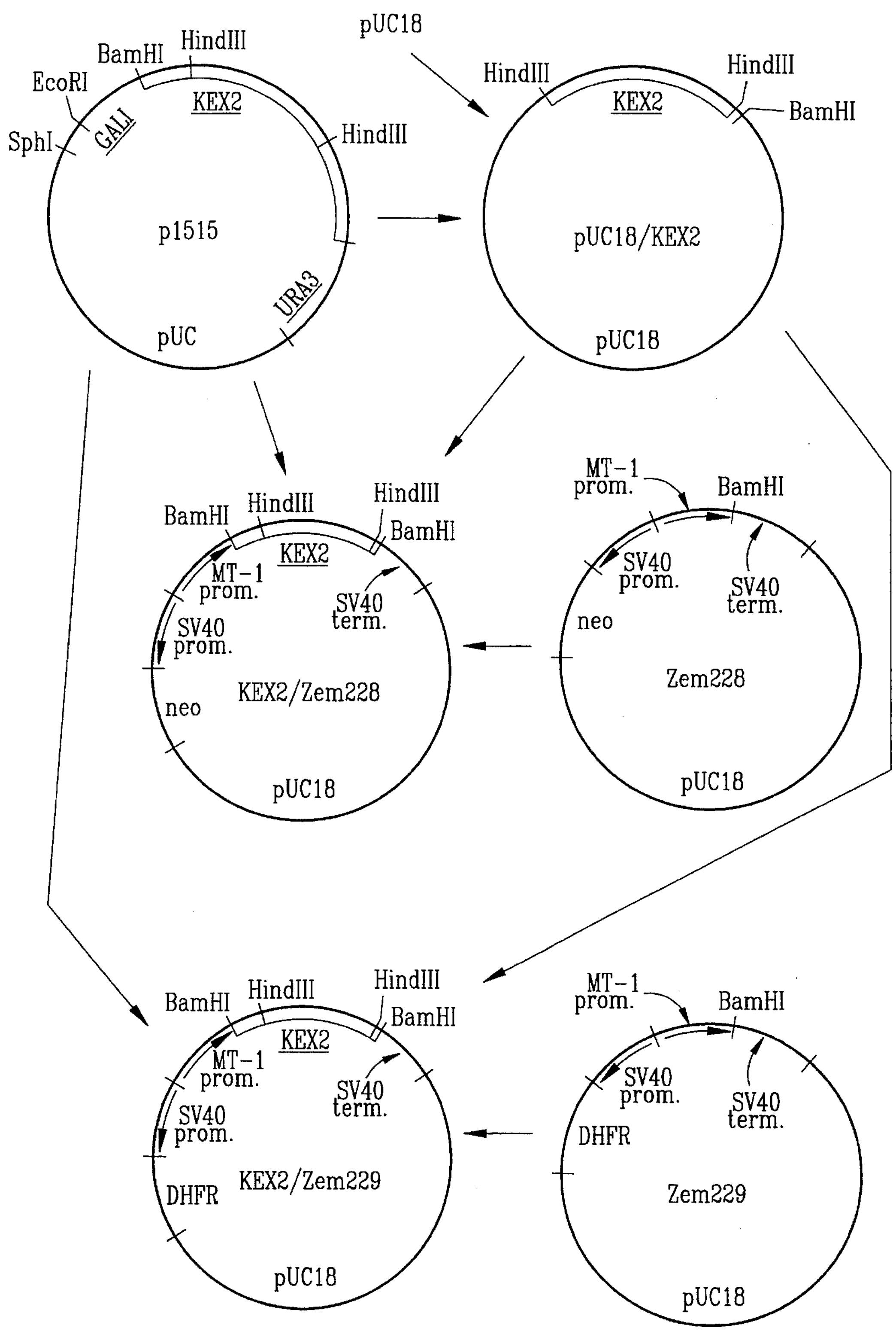
FIG. 11 illustrates the construction of plasmids containing *S. cerevisiae* KEX2 gene.

The activity of the PC1058 protein was compared to that of activated plasma protein C and activated PC962. Plasma protein C and PC962 (5 μg/ml) were activated by treatment with 1/10 volume Protac C (American Diagnostica) for 2 hours. Anticoagulant activity was assayed by combining 50 μl human plasma with 50 μl of the samples containing activated protein C and incubating the mixtures at 37° C. for 150 seconds. To the mixtures was added 50 μl activated cephaloplastin (American Scientific Products, McGaw Park, Ill.), and the mixtures were incubated at 37° C. for 300 seconds. One hundred μl of 20 mM $CaCl_2$ was added and the clotting times were recorded. Data are presented in FIG. 10.

C. Expression of Activated Protein C from pDX/PC1058 in a KEX2 Transfected Cell Line The *Saccharomyces cerevisiae* KEX2 gene was isolated from a yeast genomic library by screening transformed kex2 mutant cells for production of an α-factor halo on a lawn of a suitable tester cells. One clone was obtained that complemented all reported defects of kex2 mutants (mating, α-factor production, maturation of killer toxin and sporulation in a homozygous diploid strain). The gene was subcloned into a pUC vector under the control of the yeast GAL1 promoter. The resultant plasmid, designated p1515, has been deposited with American Type Culture Collection under accession number 67569. As shown in FIG. 12, p1515 was digested with Hind III, and a 2.1 kb fragment was recovered. This fragment was ligated to Hind III-cut pUC18 to construct plasmid pUC18/KEX2. The KEX2 fragment (2.1 kb) was then isolated from pUClS/KEX2 by digesting the plasmid partially with Hind III and to completion with Bam HI. The remainder of the KEX2 sequence was then isolated as a 0.43 kb fragment from a Bam HI+Hind III digest of p1515. The two KEX2 fragments were then ligated into the Bam HI site of the vectors Zem228 and Zem229. (Zem228 is similar to Zem229 but contains a neomycin resistance gene in place of the DHFR gene. Thus, in Zem228 the inserted gene is under the control of the metallothionein-1 promoter and SV40 terminator, and the vector can be selected with the antibiotic G418.) The resulting plasmids were designated KEX2/Zem228 and KEX2/ZEM229, respectively A high protein C producing pDX/PC1058-transfected $tk^{-}$ts13 BHK clone (pDX/PC1058-3//BHK) was identified as described in Example 4.A. The clone pDX/PC1058-3//BHK was transfected with KEX2/Zem228 by the calcium phosphate procedure. Transfected cells were selected with 500 μg/ml G418 and 250 nM methotrexate.

A selected clone, designated KEX2-1058//BHK, was pulse-labeled with $^{35}$S-cysteine in cysteine-free DMEM (Gibco) containing 1% fetal calf serum for 24 hours. The culture media were collected and were assayed for the presence of single-chain and two-chain protein C by immunoprecipitation with a monoclonal antibody to protein C. Two hundred and fifty μl of media was combined with 10 μg of antibody, and the mixture was incubated at 37° C. for one hour. One hundred μl of Staph A cell suspension (Pharmacia, Piscataway, N.J.) was added, and the mixture was incubated at 37° C. for one hour. The cells were pelleted by centrifugation, and the pellet was resuspended in 60 μl of gel buffer containing 1% β-mercaptoethanol. The suspension was heated to 100° C. for three minutes, then electrophoresed on an SDS-polyacrylamide gel. Proteins were visualized by autoradiography. The KEX2-1058//BHK clone showed approximately 100% cleavage of the protein into the two-chain form.

Protein C was isolated from the KEX2-1058//BHK clone that was grown in DMEM supplemented with 10% fetal calf serum, 250 nM methotrexate and 500 μg/ml G418 until the cells reached confluency. The confluent cells were switched to DMEM supplemented with 1 μg/ml fibronectin, 2 μg/ml insulin, 5 μg/ml transferrin, 5 μg/ml vitamin K, 1× PSN antibiotic mix (Gibco 600–5640), 2.0 mM L-glutamine, 250 nM methotrexate and 500 μg/ml G418. Media were collected every 1 to 2 days over a period of 7 days and were frozen at −20° C. The frozen media samples were thawed and filtered through 0.45 μm filters to remove any cell debris. Calcium chloride was added to a final concentration of 5 mM, and sodium azide was added to a final concentration of 0.02% (weight/volume). Protein C was purified from the media using a monoclonal antibody column specific for the calcium-induced conformation of protein C. The treated media samples were applied to the column, and protein C was eluted with TBS containing 10 mM EDTA. Protein C concentration was determined by absorbance at 280 nm and by ELISA (Example 2.C.).

Protein C activity was measured by an anticoagulant activity assay. Affinity purified plasma protein C was incubated with ACC-C (*Agkistrodon contortrix contortrix* protease [Kisiel et al., *J. Biol. Chem.* 262:12607–12613, 1987] obtained from W. Kisiel, University of New Mexico, Albuquerque, N. Mex.) diluted in 50 mM Tris, 100 mM NaCl and 0.1% bovine seum albumin at a ratio of 500:1 (APC:ACC-C) for 2 hours at 37° C. Affinity purified protein C from KEX2-1058//BHK cells was incubated for 2 hours at 37° C. Clot formation was measured in an MLA Electra 800 Coagulation Timer (Medical Laboratory Automation, Inc., Pleasantville, N.Y.). One hundred μl of activated plasma protein C or KEX2-1058 protein C was added to an MLA cuvette and warmed for 50 seconds to raise the temperature to 37° C. One hundred μl of Dade Actin FS (American Scientific Products) was added, and the test solutions were incubated for 100 seconds. One hundred μl of 25 mM $CaCl_2$ was added to each cuvette. The time required for clot formation was measured. Results of coagulation assays showed that protein C produced by KEX2-1058//BHK cells is approximately 100% active relative to plasma proten C.

The carboxy-terminal sequence of the light chain of KEX2-1058 protein C was determined using CNBr cleavage at the unique methionine residue of the light chain to liberate a peptide that was sequenced in its entirety by N-terminal sequence analysis. Affinity-purified protein C from KEX2-1058//BHK cells grown in DMEM supplemented with 1% fetal calf serum, 250 nM methotrexate and 500 μg/ml G418 was first reduced by the addition of a 10-fold molar excess per Cys residue of dithiolthreitol (DTT) in 0.2M Tris-HCl, pH8.3, and guanidine-HCl to a final concentration of 6.0M. The mixture was incubated at 65° C. for 4–6 hours. Iodoacetic acid pH 7.0 or iodoacetic amide was added to the reduced protein in a four-fold molar excess over the molar concentration of DTT, and the mixture was incubated for 30 minutes at 37° C. The solution was dialized against 0.1M $NH_4HCO_3$, pH 8.5 for 24 hours at 22° C. The dialized solution was applied to an HPLC Poly-F column (DuPont) to isolate the light chain. A 500-fold molar excess per methionine residue of CNBr was added to the purified light chain in 70% formic acid under nitrogen for 30 hours at room temperature in the dark. The CNBr digest was applied to an American Biosystems Inc. Model 470A sequenator (American Biosystems Inc., Marine-on-St. Croix, Minn.). Surprisingly, the resultant sequence analysis showed that the C-terminal sequence of both the commercially available purified protein C and the KEX2-1058 protein ended with Glu, indicating that the light chains of both proteins terminate at amino acid 149.

D. Expression of Activated Protein C from pPC1962/ZMB-2 in KEX2 Transfected Cells The coding sequence of protein C was altered to remove amino acids 153–169, resulting in an activated protein C precursor with a light chain-heavy chain junction between amino acids 152 and 170. The sequence of this activated protein C precursor, designated 1962, is presented in Table 2.

Oligonucleotide-directed mutagenesis was carried out on a template comprising the Sst I fragment of p594 inserted, in the proper orientation, into the Sst I site of M13mp10. Single-stranded template DNA was prepared from the 594/mp10 phage clone. Oligonucleotide-directed mutagenesis was carried out on the template using the synthetic oligonucleotides ZC1962 (5' GAG AAG AAG CGC CTC ATT GAT GGG 3') and ZC550. Positive phage clones were sequenced to confirm the mutagenesis. A positive phage clone was designated 1962.

Replicative form DNA was prepared from phage clone 1962 and was digested with Sst I and Pst I to isolate the approximately 0.4 kb mutagenized fragment. Plasmid PC229/962 was digested with Eco RI and Pst I to isolate the 562 bp protein C fragment. A 700 bp Sst I-Eco RI protein C fragment was obtained from PC1869/229R (a plasmid comprising a protein C coding sequence similar to p594 with the Arg codon (residue 157) substituted with a Lys codon inserted into the Eco RI site of Zem229R.) Plasmid pZMB-2 (FIG. 12) was linearized by digestion with Eco RI. (Plasmid pZMB-2 is similar to Zem229R but contains the SV40 enhancer, Adenovirus 2 major late promoter, Adenovirus 2 tripartite leader, and 5' and 3' splice sites substituted for the MT-1 promoter using an Sst I-Hind III adapter.) The approximately 0.4 kb Pst I-Sst I fragment from phage clone 1962, the 700 bp Pst I-Eco RI fragment from PC1869/229R, the 562 bp Sst I-Eco RI fragment from PC229/962 and the linearized pZMB-2 were joined in a four-part ligation. A plasmid with the insert in the correct orientation was designated pPC1962/ZMB-2.

Plasmid pPC1962/ZMB-2 was transfected into $tk^{-}$ts13 BHK cells by calcium phosphate co-precipitation. Transfected cells were grown in DMEM containing 10% fetal calf serum, 1× PSN antibiotic mix (Gibco), 2.0 mM L-glutamine and 5 μg/ml vitamin K. The cells were selected in 500 nM methotrexate for 15 days, and the resulting colonies were screened by an immunofilter assay (Example 3.B.). The most intensely reacting colonies were picked by cylinder cloning and were grown individually in 10 cm plates. When the cultures were nearly confluent, protein C production levels were measured by ELISA (Example 2.C.).

A high protein C producing pPC1962/ZMB-2 transfectant was transfected with KEX2/ZMB-1. (KEX2/ZMB-1 comprises the KEX2 coding sequence inserted into the vector ZMB-1 at the unique Eco RI site. ZMB-1, as shown in FIG. 12, is similar to ZMB-2 but was constructed from Zem228R.) Co-transfected cells were selected and media samples were collected. Activated protein C was dectected in media samples from pPC1962-KEX2/ZMB-1 co-transfected cells.

E. Construction and Expression of pPC1645/Zem229R.

A DNA sequence encoding amino acids Arg-Arg-Lys was substituted for the DNA sequence encoding amino acids 9–11 of the activation peptide present in plasmid p962. The amino acid sequence at the junction between the light and heavy chains of the encoded protein (designated 1645) is presented in Table 2.

Plasmid p962 was digested with Sal I and Sst I, and the purified 730 bp fragment was inserted into M13mp10 that had been linearized by digestion with Sal I and Sst I. Synthetic oligonucleotides ZC1645 (5' GAA GAC CAA ACA ACA AAA CGG CTC ATT GAT 3') and ZC550 were used to mutagenize the single-stranded template DNA by site-directed in vitro mutagenesis (Zoller and Smith, ibid.). The mutant phage clones were subjected to dideoxy-sequencing to confirm the mutagenesis. Replicative form (rf) DNA from a confirmed mutant phage clone, designated 1645, was prepared and was digested with Sst I and Pst I to isolate the 411 bp fragment. Plasmid PC229/962 (Example 3.B.) was digested with Eco RI and Pst I to isolate the 592 bp protein C fragment. Plasmid PC229/962 was also digested with Eco RI and Sst I to isolate the 700 bp protein C fragment. The 411 bp protein C fragment from the 1645 rf, the 411 bp protein C fragment from PC229/962, and the 700 bp protein C fragment were joined in a four-part ligation with Zem229R that had been linearized with Eco RI and treated with calf intestinal phosphatase to prevent self-ligation. (Plasmid Zem229R is similar to Zem229 except that the Eco RI sites present in Zem299 have been destroyed by partial digestion, blunt ending by treatment with DNA polymerase I (Klenow fragment) dNTP's and religation, and a unique Eco RI site was created at the Bam HI site by digestion with Bam HI and religation with Bam HI-Eco RI adapters.) A correct plasmid was selected and was designated pPC1645/229R.

Plasmid pPC1645/229R was transfected into $tk^-$ts13 BHK cells by calcium phosphate co-precipitation (Graham and van der Eb, *Virology* 53:456–467, 1973). Transfected cells were subjected to selection with 1 μM methotrexate and media were assayed for protein C by ELISA (Example 2.C.). A positive clone was grown in DMEM supplemented with 10% fetal calf serum and 1 μM methotrexate until the cells reached confluency. The confluent cells were switched to DMEM supplemented with 1% fetal calf serum and 1 μM methotrexate. Media were collected every 1 to 2 days over a period of 7 days and was frozen at −20° C. The frozen media samples were thawed and filtered through 0.45 μm filters to remove any cell debris. Solid calcium chloride was added to a final concentration of 5 mM and solid sodium azide was added to a final concentration of 0.02% (weight/volume). Protein C was purified from the media using a monoclonal antibody column specific for the calcium-induced conformation of protein C. The treated media samples were applied to the column, and protein C was eluted with TBS containing 10 mM EDTA. Protein C concentrations were determined by absorbance at 280 nm and by ELISA (Example 2.C.).

Activated protein C produced from pPC1645/229R-transfected cells was compared to an equivalent amount of PC229/962 protein C using a chromogenic assay. One μg of affinity-purified protein C diluted in 40 μl TBS+EDTA was added to each well of a 96-well plate. Forty μl of 2 mM Spectrozyme PCa (American Diagnostica Inc, New York, N.Y.) was added to each well and incubated at 37° C. until there was sufficient color development. Activity was measured as an increase in absorbance at 405 nm. The results showed that the activated protein C produced from pPC1645/229R-transfected cells was 5–10% more active than the PC229/962 produced protein C.

F. Construction and Expression of pPC1880/229R.

The DNA sequence encoding protein C in plasmid 1645 was further modified to remove the first, second, seventh and eighth amino acids of the activation peptide. Single-stranded 1645 template DNA was prepared and was subjected to site-directed in vitro mutagenesis (Zoller and Smith, ibid.) using synthetic oligonucleotides ZC1880 (5'AAA CGA GAC ACA GAC CAA AGA AGA 3') and ZC550. Positive phage clones were subjected to dideoxy sequencing to confirm the mutagenesis. A positive clone was identified and was designated 1880 (Table 2).

Replicative form DNA prepared from clone 1880 was digested with Sst I and Pst I to isolate the approximately 0.4 kb fragment. Plasmid PC229/962 was digested with Eco RI and Pst I to isolate the 562 bp protein C fragment Plasmid PC229/962 was also digested with Eco RI and Pst I to isolate the 700 bp protein C fragment. The 411 bp protein C fragment from the 1880 rf, the 700 bp and 562 bp fragments from PC229/962 and Eco RI digested Zem229R were joined in a four-part ligation. A correct plasmid was selected and was designated pPC1880/229R.

Plasmid pPC1880/229R was transfected into $tk^-$ ts13 BHK cells. Media samples from transfected cells showed that activated protein C was produced.

G. Construction and Expression of pPC1954/229R.

The coding sequence of the activation peptide present in plasmid 1645 is altered to remove the second through seventh amino acid codons of the activation peptide, resulting in a fusion between the first and eighth amino acid codons of the activation peptide present in 1645 (Table 2). Single-stranded 1645 template DNA is prepared and subjected to site directed in vitro mutagenesis using the synthetic oligonucleotides ZC1954 (5' GAG AAG AAA ACG AGA CCA AAG AAG AAA AC 3') and ZC550. Positive clones are sequenced to confirm the mutagenesis. A positive clone is selected and is designated 1954 (Table 2).

Replicative form DNA is prepared from 1954 and digested with Sst I and Pst I to isolate the approximately 400 bp mutagenized protein C fragment. Plasmid PC229/962 is digested with Eco RI and Pst I and with Sst I and Eco RI to isolate the 562 bp Eco RI-Pst I fragment and the 700 bp protein C fragment. The approximately 0.4 kb protein C fragment from the 1954 rf, the 700 bp and 562 bp fragments from pPC229/962 and Eco RI-digested pZem229R are joined in a four-part ligation. A correct plasmid is selected and designated pPC1954/229R.

Plasmid pPC1954/229R is transfected into $tk^-$ts13 BHK cells by calcium phosphate co-precipitation (Graham and van der Eb, ibid.). Cells are selected and assayed for the production of activated protein C.

H. Construction and Expression of pPC1953/229R.

The coding sequence of the activation peptide present in plasmid 1645 is altered to remove the first through eighth amino acid codons of the activation peptide, resulting in a fusion between the first and second sets of Arg-Arg-Lys-Arg amino acid codons present in 1645. The amino acid sequence at the light-heavy chain junction of the encoded protein (designated 1953) is shown in Table 2.

Single-stranded 1645 template DNA is prepared and is subjected to site directed in vitro mutagenesis using the synthetic oligonucleotides ZC1953 (5' ACC TCA GAA GAA AAC GAA GAA GAA AAC GGC TCA T 3') and ZC550. Positive clones are sequenced to confirm the mutagenesis. A positive clone is selected and is designated 1953. Replicative form DNA is prepared from clone 1953 and is digested with Sst I and Pst I to isolate the approximately 0.4 kb mutagenized protein C fragment. Plasmid PC229/962 is digested with Eco RI and Pst I or Sst I and Eco RI to isolate the 562 bp Eco RI-Pst I fragment and the 700 bp protein C fragment. The approximately 400 bp protein C fragment from the 1953 rf, the 700 bp and 562 bp fragments from PC229/962 and Eco RI digested Zem229R are joined in a four-part ligation. A correct plasmid is selected and designated pPC1953/229R Plasmid pPC1953/229R is transfected into tk$^-$ts13 BHK cells by calcium phosphate co-precipitation (Graham and van der Eb, ibid.). Cells are selected and assayed for the production of activated protein C.

I. Construction of pPC2043/ZMB-2

An activated protein C precursor is constructed in which the sequence encoding the activation peptide is removed and an Arg codon is inserted between amino acid codons 150 and 151 of native protein C. The amino acid sequence at the light-heavy chain junction of the encoded protein (designated 2043) is shown in Table 2.

Single stranded template DNA is prepared from phage clone 1962 and subjected to site-directed in vitro mutagenesis using the synthetic oligonucleotides ZC2043 (5' AGC CGG ATG GAG AAG AGG AAG CGC CTC ATT GC 3') and ZC550. Positive clones are sequenced to confirm the mutagenesis. Replicative form DNA is prepared from a confirmed phage clone and is digested with Pst I and Sst I to isolate the approximately 0.4 kb mutagenized fragment. Plasmid PC229/962 is digested with Eco RI and Pst I and with Sst I and Eco RI to isolate the 562 Eco RI-Pst I protein C fragment and the 700 bp Eco RI-Sst I protein C fragment, respectively. Plasmid ZMB-2 is linearized by digestion with Eco RI. The 0.4 kb Pst I-Sst I fragment is joined with the 562 bp Eco RI-Pst I fragment, the 700 bp Sst I-Eco RI fragment and the linearized ZMB-2 in a four part ligation. A plasmid containing the insert in the correct orientation is designated pPC2043/ZMB-2.

Plasmid pPC2043/ZMB-2 is transfected into tk$^-$ts13 BHK cells. Transfected cells are assayed for the production of activated protein C.

EXAMPLE 5

Use of the Factor VII and Prothrombin Pre-Pro Peptides to Secrete Protein C

The protein C sequence was isolated from p594 by partial cleavage with Sst I and complete digestion with Eco RI. A 1540 bp fragment extending from the Sst I site at codon +7 to the Eco RI site 3' to the cDNA was isolated.

The factor VII and protein C sequences were then joined by means of an oligonucleotide linker that completes the coding sequence for amino acids −3 to −1 of the factor VII pre-pro peptide and amino acids 1–8 of protein C. The linker was constructed from two oligonucleotides having the sequences 5'CCG GCG CGC CAA CTC CTT CCT GGA GGA GCT 3' and 5'CCT CCA GGA AGG AGT TGG CGC GCC GGC G 3'. The two oligonucleotides were annealed and joined in a four-part ligation to the factor VII pre-pro sequence, protein C eDNA and pUC9, which had been cleaved with Eco RI and treated with bacterial alkaline phosphatase. The ligated DNA was used to transform *E. coli* JM101. Plasmid DNA was prepared and screened for the presence of a 1710 bp Eco RI fragment. A correct clone was designated p7/C-10.

The factor VII/protein C fusion was expressed in 293 cells. The Eco RI insert from plasmid p7/C-10 was ligated to Eco RI-digested pDX. The resulting expression vector was used to co-transfect 293 cells as previously described. Forty-eight hour expression levels were assayed by ELISA and compared to those of 293 cells transfected with the wild-type protein C expression construct and untransfected cells. Results are presented in Table 5.

TABLE 5

| Protein | ng/ml |
|---|---|
| Factor VII/protein C | 123 |
| Wild-type protein C | 187 |
| Control | <1 |

The prothrombin leader sequence was constructed from the oligonucleotides listed in Table 6 and was fused to the mature protein C coding sequence. Fifty ng of each oligonucleotide was kinased using essentially the method described by Maniatis et al. (ibid.).

TABLE 6

| | | | | | | | | | | | | |
|---|---|---|---|---|---|---|---|---|---|---|---|---|
| ZC1323 | 5' | CCT | CCA | GGA | AGG | ACT | TGG | CTC | GCC | GGA | 3' | |
| ZC1324 | 5' | CGC | GTC | CGG | CGA | GCC | AAC | TCC | TTC | CTG | GAG | GAG |
| | | CT | 3' | | | | | | | | | |
| ZC1378 | 5' | AAT | TCC | ACC | ATG | GCT | CAT | GTG | AGA | GGA | CTG | CAA |
| | | CTG | CCT | GGC | TGC | CTG | GCT | CTG | GCT | GCT | CTG | TGC |
| | | AGC | CTG | GTG | CAC | AGC | CAG | CAT | GTG | TTC | CTG | GCT |
| | | CCT | CAG | CAG | GCC | AGG | AGC | CTG | CAA | 3' | | |
| ZC1379 | 5' | CGC | GTT | GCA | GCA | GGC | TCCC | TGG | CCT | GCT | GAG | GAG |
| | | CCA | GGA | ACA | CAT | GCT | GGC | TGT | GCA | CCA | GGC | TGC |
| | | ACA | GAG | CAG | CCA | GAG | CCA | GGC | AGC | CAG | GCA | GTT |
| | | GCA | GTC | CTC | TCA | CAT | GAG | CCA | TGG | TGG | 3' | |

The factor VII pre-pro peptide was substituted for the protein C pre-pro peptide in an effort to obtain higher yields of properly processed protein C. The hybrid construct was then inserted into an expression vector and transfected into cultured mammalian cells.

A cDNA encoding factor VII has been described (Hagen et al., *Proc. Natl. Acad. Sci. USA* 83:2412–2416, 1986). Clone λHVII565 comprises the coding sequence for a 38 amino acid pre-pro peptide. This coding sequence was isolated as an Eco RI-Hha I fragment of 140 bp.

The prothrombin leader was then assembled. Fifty ng of Eco RI-Sst I-cut M13mp19 and 2.5 ng each of the kinased oligonucleotides were joined by ligation, and the mixture was transformed into *E. Coli* JM101 cells. A clear plaque was selected and phage DNA was prepared. DNA sequencing confirmed that the correct sequence had been constructed. The prothrombin leader was then joined to the protein C sequence. Replicative form DNA was prepared from the phage clone containing the synthesized leader and a 150 bp Eco RI-Sst I fragment was isolated. Plasmid p594 was digested to completion with Eco RI and partially digested with Sst I and the 1540 bp protein C fragment was recovered. These fragments were ligated with Eco RI-cut pDX, and the ligation mixture was used to transform *E. coli* HB101 cells. Plasmid DNA was isolated from transformant colonies and was analyzed by restriction digestion to confirm that the fragments had been assembled in the correct orientation.

From the foregoing it will be appreciated that, although specific embodiments of the invention have been described herein for purposes of illustration, various modification may be made without deviating from the spirit and scope of the invention. Accordingly, the invention is not limited except as by the appended claims.

We claim:

1. An isolated DNA sequence which codes for human protein C or human activated protein C, said sequence further coding for the amino acid sequence $(R_1)_n$-$R_2$-$R_3$-$R_4$, wherein each of $R_1$, $R_2$, $R_3$ and $R_4$ is Lys or Arg and n=1, 2 or 3, between the light and heavy chains.

2. A DNA sequence which codes for a pre-pro peptide of a human protein selected from the group consisting of factor VII, factor IX, factor X, prothrombin and protein S, positioned upstream of and operably linked to a DNA sequence which codes for human protein C or human activated protein C.

3. A DNA sequence which codes for human protein C or human activated protein C, said protein further including the substitution of residue 158 as shown in FIG. 2 with a non-acidic amino acid residue selected from the group consisting of Ala, Ser, Thr, and Gly.

4. A DNA sequence which codes for human protein C or human activated protein C, said protein further including the substitution of residue 154 as shown in FIG. 2 with an amino acid residue selected from the group consisting of Lys, Arg and Leu.

5. A DNA sequence which codes for human protein C or human activated protein C, said protein further including the substitution of Lys-Arg at residues 156–157 as shown in FIG. 2 with Lys-Lys or Arg-Arg.

6. A DNA sequence which codes for human activated protein C, said sequence further coding for the amino acid sequence $R_1$-$R_2$-$R_3$-$R_4$-X-$R_5$-$R_6$-$R_7$-$R_8$, wherein each of $R_1$–$R_8$ is Lys or Arg and X is a peptide bond or a spacer peptide of 1–12 amino acids, between the light and heavy chains.

7. The DNA sequence of claim 6 wherein said spacer peptide is selected from the group consisting of Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln, and Asp-Gln.

8. A DNA sequence which codes for human activated protein C, said sequence coding for the amino acid sequence L-$R_1$-$R_2$-$R_3$-$R_4$-X-$R_5$-$R_6$-$R_7$-$R_8$-H, wherein L is the light chain of protein C, each of $R_1$–$R_8$ is Lys or Arg, X is a peptide bond or a spacer peptide of 1–12 amino acids, and H is the heavy chain of activated protein C.

9. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said sequence further coding for the amino acid sequence $(R_1)_n$-$R_2$-$R_3$-$R_4$, wherein each of R1, R2, R3 and R4 is Lys or Arg and n=1, 2 or 3, between the light and heavy chains.

10. The cells of claim 9 wherein said cells are selected from the group consisting of $tk^-ts13$ BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

11. The cells of claim 10 wherein said cells are further transfected with the KEX1 or KEX2 gene of *Saccharomyces cerevisiae.*

12. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C.

13. The cells of claim 12 wherein said cells are selected from the group consisting of $tk^-ts13$ BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

14. Cultured mammalian cells stably transfected with an expression vector, said expression vector including a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of residue 158 as shown in FIG. 2 with a non-acidic amino acid residue selected from the group consisting of Ala, Ser, Thr and Gly.

15. The cells of claim 14 wherein said cells are selected from the group consisting of $tk^-ts13$ BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

16. The cells of claim 14 wherein said cells are further transfected with the KEX1 or KEX2 gene of *Saccharomyces cerevisiae.*

17. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of residue 154 as shown in FIG. 2 with an amino acid residue selected from the group consisting of Lys, Arg and Leu.

18. The cells of claim 17 wherein said cells are selected from the group consisting of $tk^-ts13$ BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

19. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of Lys-Arg at residues 156–157 as shown in FIG. 2 with Lys-Lys or Arg-Arg.

20. The cells of claim 19 wherein said cells are selected from the group consisting of $tk^-ts13$ BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

21. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said cells further transfected with the KEX1 or KEX2 gene of *Saccharomyces cerevisiae.*

22. The cells of claim 21 wherein said cells are selected from the group consisting of tk⁻ts13 BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

23. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human activated protein C, said sequence further coding for the amino acid sequence $(R_1)_n$-$R_2$-$R_3$-$R_4$, wherein each of $R_1$, $R_2$, $R_3$ and $R_4$ is Lys or Arg and n=0, 1, 2 or 3, between the light chain and the heavy chain, said cells further transfected with the KEX1 or KEX2 gene of *Saccharomyces cerevisiae.*

24. The cells of claim 23 wherein said cells are selected from the group consisting of tk⁻ts13 BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

25. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human activated protein C, said sequence further coding for the amino acid sequence $R_1$-$R_2$-$R_3$-$R_4$-X-$R_5$-$R_6$-$R_7$-$R_8$, wherein each of $R_1$–$R_8$ is Lys or Arg and X is a peptide bond or a spacer peptide of 1–12 amino acids, between the light and heavy chains.

26. The cells of claim 25 wherein said spacer peptide is selected from the group consisting of Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln, and Asp-Gln.

27. The cells of claim 25 wherein said cells are selected from the group consisting of tk⁻ts13 BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

28. A method for producing human protein C or human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of residue 158 as shown in FIG. 2 with a non-acidic amino acid residue selected from the group consisting of Ala, Ser, Thr and Gly;

growing said cultured mammalian host cell in an appropriate growth medium; and isolating the protein encoded by said expression vector and produced by said mammalian host cell.

29. The cells of claim 28 wherein said cells are selected from the group consisting of tk⁻ts13 BHK cells, 293 cells, COS-1 cells, Rat Hep I cells, Rat Hep II cells, TCMK cells, Human lung cells, Human hepatoma cells, Hep G2 cells, Mouse liver cells and DUKX cells.

30. The method of claim 28 wherein said cell is further transfected with the KEX1 or KEX2 gene of *Saccharomyces cerevisiae.*

31. A method for producing human protein C or human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of residue 155 as shown in FIG. 2 with an amino acid residue selected from the group consisting of Lys, Arg and Leu;

growing said cultured mammalian host cell in an appropriate growth medium; and isolating the protein encoded by said expression vector and produced by said mammalian host cell.

32. The method of claim 31 wherein said cell is selected from the group consisting of a tk⁻ts13 BHK cell, 293 cell, COS-1 cell, Rat Hep I cell, Rat Hep II cell, TCMK cell, Human lung cell, Human hepatoma cell, Hep G2 cell, Mouse liver cell and DUKX cell.

33. A method for producing human protein C or human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said DNA sequence further coding for the amino acid sequence $(R_1)_n$-$R_2$-$R_3$-$R_4$, wherein each of $R_1$, $R_2$, $R_3$ and $R_4$ is Lys or Arg and n=1, 2 or 3, between the light and heavy chains;

growing said cultured mammalian host cell in an appropriate growth medium; and isolating the protein encoded by said expression vector and produced by said cultured mammalian host cell.

34. The method of claim 33 wherein said cell is selected from the group consisting of tk⁻ts13 BHK cell, 293 cell, COS-1 cell, Rat Hep I cell, Rat Hep II cell, TCMK cell, Human lung cell, Human hepatoma cell, Hep G2 cell, Mouse liver cell and DUKX cell.

35. The method of claim 33 wherein said cell is further transfected with the KEX1 of KEX2 gene of *Saccharomyces cerevisiae.*

36. A method for producing human protein C or human activated protein C, comprising:

introducing into a cultured mammalian host cell an expression vector capable of directing the expression of a cloned gene in a mammalian cell, said expression vector comprising a DNA sequence which codes for a pre-pro peptide of a human protein selected from the group consisting of factor VII, factor IX, factor X, prothrombin and protein S, positioned upstream from a promoter, the promoter being operably linked to a DNA sequence which codes for human protein C or human activated protein C;

growing said cultured mammalian host cell in an appropriate growth medium; and isolating the protein encoded by said expression vector and produced by said cultured mammalian host cell.

37. The method of claim 36 wherein said cell is selected from the group consisting of $tk^{-}ts13$ BHK cell, 293 cell, COS-1 cell, Rat Hep I cell, Rat Hep II cell, TCMK cell, Human lung cell, Human hepatoma cell, Hep G2 cell, Mouse liver cell and DUKX cell.

38. A method for producing human protein C or human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said protein further including the substitution of Lys-Arg at residues 156–157 as shown in FIG. 2 with Lys-Lys or Arg-Arg;

growing said cultured mammalian host cell in an appropriate growth medium; and isolating the protein encoded by said expression vector and produced by said cultured mammalian host cell.

39. The method of claim 38 wherein said cell is selected from the group consisting of $tk^{-}ts13$ BHK cell, 293 cells, COS-1 cell, Rat Hep I cell, Rat Hep II cell, TCMK cell, Human lung cell, Human hepatoma cell, Hep G2 cell, Mouse liver cell and DUKX cell.

40. A method for producing human protein C or human activated protein C, comprising:

transfecting a cultured mammalian host cell with an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said cell further transfected with the KEX1 or KEX2 gene of *Saccharomyces cerevisiae;* growing said cultured mammalian host cell in an appropriate growth medium; and isolating the protein encoded by said expression vector and produced by said cultured mammalian host cell.

41. The method of claim 40 wherein said cell is selected from the group consisting of $tk^{-}ts13$ BHK cell, 293 cell, COS-1 cell, Rat Hep I cell, Rat Hep II cell, TCMK cell, Human lung cell, Human hepatoma cell, Hep G2 cell, Mouse liver cell and DUKX cell.

42. A method for producing activated protein C, comprising:

transfecting a cultured mammalian host cell with an expression vector capable of directing the expression of a cloned gene in a mammalian cell, said expression vector comprising a promoter operably linked to a DNA sequence which codes for a pre-pro peptide of a human protein selected from the group consisting of Protein C, Factor VII, Factor IX, Factor X, prothrombin, and protein S, operably linked to a DNA sequence which codes for human activated protein C, said sequence further coding for the amino acid sequence $R_1$-$R_2$-$R_3$-$R_4$-X-$R_5$-$R_6$-$R_7$-$R_8$, wherein each of $R_1$–$R_8$ is Lys or Arg and X is a peptide bond or a spacer peptide of 1–12 amino acids, between the light and heavy chains;

growing said cultured mammalian host cell in an appropriate growth medium; and isolating the protein encoded by said expression vector and produced by said cultured mammalian host cell.

43. The method of claim 42 wherein said spacer peptide is selected from the group consisting of Asp-Thr-Glu-Asp-Gln-Glu-Asp-Gln-Val-Asp-Pro, Asp-Thr-Glu-Asp-Gln-Glu-Asp-Gln, Asp-Thr-Asp-Gln, and Asp-Gln.

44. The method of claim 42 wherein said cell is selected from the group consisting of $tk^{-}ts13$ BHK cell, 293 cell, COS-1 cell, Rat Hep I cell, Rat Hep II cell, TCMK cell, Human lung cell, Human hepatoma cell, Hep G2 cell, Mouse liver cell and DUKX cell.

45. A DNA sequence which codes for human protein C or human activated protein C, said sequence further coding for the amino acid sequence $(R_1)_n$-$R_2$-$R_3$, wherein each of $R_1$, $R_2$ and $R_3$ is Lys or Arg and n=1, 2 or 3, between the light chain of protein C, as shown in FIG. 2 from amino acid residue 1 to residue 155, and the heavy chain of protein C.

46. Cultured mammalian cells transfected with an expression vector capable of integration into mammalian cell DNA, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said sequence further coding for the amino acid sequence $(R_1)_n$-$R_2$-$R_3$, wherein each of $R_1$, $R_2$ and $R_3$ is Lys or Arg and n=1, 2 or 3, between the light chain of protein C, as shown in FIG. 2 from amino acid residue 1 to residue 155, and the heavy chain of protein C.

47. A method for producing human protein C or human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin, and protein S, operably linked to a DNA sequence which codes for human protein C or human activated protein C, said DNA sequence further coding for the amino acid sequence $(R_1)_n$-$R_2$-$R_3$, wherein each of $R_1$, $R_2$ and $R_3$ is Lys or Arg and n=1, 2 or 3, between the light chain of protein C, as shown in FIG. 2 from amino acid residue 1 to residue 155, and the heavy chain of protein C;

growing said cultured mammalian host cell in an appropriate growth medium; and isolating the protein encoded by said expression vector and produced by said cultured mammalian host cell.

48. An isolated DNA sequence which codes for human activated protein C, said DNA sequence further coding for the amino acid sequence $(R_1)_n$-$R_2$-$R_3$-$R_4$, wherein each of $R_1$, $R_2$, $R_3$, and $R_4$ is Lys or Arg and n=0, 1, 2 or 3, between the light and heavy chains.

49. Cultured mammalian cells stably transfected with an expression vector, said expression vector comprising a promoter operably linked to a DNA sequence which codes for a pre-pro peptide of a human protein selected from the group consisting of protein C, factor VII, factor IX, factor X, prothrombin and protein S, operably linked to a DNA sequence which codes for human activated protein C, said DNA sequence further coding for the amino acid sequence $(R_1)_n$-$R_2$-$R_3$-$R_4$, wherein each of $R_1$, $R_2$, $R_3$ and $R_4$ is Lys or Arg and n=0, 1, 2 or 3, between the light and heavy chains.

50. A method for producing human activated protein C, comprising:

introducing into a cultured mammalian host cell an expression vector capable of directing the expression of a cloned gene in a mammalian cell, said expression vector comprising a promoter operably linked to a DNA sequence which codes for a pre-pro peptide of a human protein selected from the group consisting of protein C, factor VII, factor IX, factor X, prothrombin and protein S, operably linked to a DNA sequence which codes for human activated protein C, said DNA sequence further coding for the amino acid sequence $(R_1)_n$-$R_2$-$R_3$-$R_4$, wherein each of $R_1$, $R_2$, $R_3$ and $R_4$ is Lys or Arg and n=0, 1, 2 or 3, between the light and heavy chains;

growing said cultured mammalian host cell in an appropriate medium; and isolating the protein encoded by said expression vector and produced by said cultured mammalian cell.

51. Cultured mammalian cells according to any of claims 9–27 and 49 wherein said pre-pro peptide is the pre-pro peptide of human protein C.

52. A method according to any of claims 28–44, 47 and 50 wherein said pre-pro peptide is the pre-pro peptide of human protein C.

* * * * *